United States Patent [19]
Ito et al.

[11] Patent Number: 5,716,965
[45] Date of Patent: Feb. 10, 1998

[54] SUBSTITUTED 3-AMINOQUINUCLIDINES

[75] Inventors: Fumitaka Ito, Chita-Taketoyo; Toshihide Kokura, Handa; Masami Nakane, Showakyu; Kunio Satake, Handa; Hiroaki Wakabayashi, Kiriya, all of Japan

[73] Assignee: Pfizer Inc., New York, N.Y.

[21] Appl. No.: 175,353

[22] PCT Filed: May 19, 1992

[86] PCT No.: PCT/US92/04002

§ 371 Date: Dec. 20, 1993

§ 102(e) Date: Dec. 20, 1993

[87] PCT Pub. No.: WO92/20676

PCT Pub. Date: Nov. 26, 1992

[30] Foreign Application Priority Data

May 22, 1991 [JP] Japan ..................... 4-046826

[51] Int. Cl.[6] .................. A61K 31/445; C07D 453/02
[52] U.S. Cl. .................. 514/305; 546/133; 546/134; 546/135; 546/136; 546/137
[58] Field of Search .................. 546/133, 137, 546/134, 135, 136; 514/305

[56] References Cited

U.S. PATENT DOCUMENTS 5,569,662 10/1996 Satake et al. .................. 514/305
5,604,241 2/1997 Ito et al. .................. 514/305

OTHER PUBLICATIONS

CA114:81592, Lowe, "Preparation of 3-amino-2 benzyl quinuclidines as substance P antagonists", PCT WO 9005525 May 31, 1990.

*Primary Examiner*—Shean C. Wu
*Attorney, Agent, or Firm*—Peter C. Richardson; Paul H. Ginsburg; Karen DeBenedicts

[57] ABSTRACT

Compounds of the formula

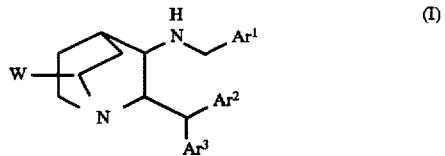

wherein W, $Ar^1$, $Ar^2$ and $Ar^3$ are defined as below; and the pharmaceutically acceptable salts of such compounds.

These compounds are substance P antagonists and useful in the treatment of gastrointestinal disorders, inflammatory disorders, central nervous system disorders and pain.

35 Claims, No Drawings

SUBSTITUTED 3-AMINOQUINUCLIDINES

This application is a 371 PCT/US 92/04002 filed May 19, 1992.

BACKGROUND OF THE INVENTION

This invention relates to novel and useful quinuclidine derivatives of interest to those in the field of medical chemistry. More particularly, it is concerned with a novel series of substituted 3-aminoquinuclidines, including their pharmaceutically acceptable salts, which are of special value in view of their ability to antagonize substance P. These compounds are useful in treating gastrointestinal disorders, central nervous system disorders, inflammatory diseases, asthma, pain and migraine. The invention also includes a new method of therapy within its scope.

E. J. Warawa, in U.S. Pat. No. 3,560,510, discloses certain 3-amino-2-benzhydryl-quinuclidines as being useful as diuretic agents, with the corresponding unsubstituted 3-benzylamino compounds acting as intermediates for same. Additionally, E. J. Warawa et al. in the Journal of Medicinal Chemistry, Vol.18, p.587 (1975) extends this work to other members of the series wherein the 3-amino moiety is ethylamino, β-phenylethylamino, β-isopropylamino, or 2-furfurylamino.

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., Journal of Medicinal Chemistry, Vol. 25, p.1009 (1982)), as well as in central nervous system disorders such as anxiety and schizophrenia, in respiratory and inflammatory diseases such as asthma and rheumatoid arthritis, respectively, and in gastrointestinal disorders and diseases of the GI tract, like ulcerative colitis and Crohn's diseases, etc. (see D. Regoli in "Trends in Cluster Headache" edited by F. Sicuteri et al., Elsevier Scientific Publishers, Amsterdam, 1987, pages 85–95).

In the recent past, some attempts have been made to provide peptide-like substances that are antagonists for substance P and other tachykinin peptides in order to more effectively treat the various disorders and diseases listed above. The peptide-like nature of such substances renders them too labile from a metabolic point of view to serve as practical therapeutic agents in the treatment of disease. The non-peptidic antagonists of the present invention, on the other hand, do not possess this drawback, being far more stable from a metabolic point of view than the peptic-like prior art agents.

Other non-peptide substance P receptor antagonists are referred to in pending patent applications assigned in common with the present application. Quinuclidine derivatives and related compounds that exhibit activity as substance P receptor antagonists are referred to in PCT Patent Application PCT/US 89/05338; filed Nov. 20, 1989 and published as WO 90/05729 on May 31, 1990, and U.S. patent application Ser. No. 557,442, filed Jul. 23, 1990. Other quinuclidine derivatives and related compounds that exhibit activity as substance P receptor antagonists are referred to in the PCT patent applications entitled "3-Amino-2-Aryl Quinuclidines" and "Quinuclidine Derivatives" and filed, respectively, on Apr. 25, 1991 and May 15, 1991. Piperidine derivatives and related heterocyclic nitrogen containing compounds that are useful as substance P antagonists are referred to in U.S. patent application Ser. No. 619,361, filed Nov. 28, 1990 and U.S. patent application Ser. No. 590,423, filed Sep. 28, 1990. Azanorbornane derivatives that exhibit activity as substance P receptor antagonists are referred to in U.S. patent application Ser. No. 07/719,884, filed Jun. 21, 1991. Fluoroalkoxy derivatives of nitrogen containing heterocycles that exhibit activity as substance P receptor antagonists are referred to in U.S. patent application Ser. No. 07/717,943, filed Jun. 20, 1991. All of the above patent applications are assigned in common with the present application.

SUMMARY OF THE INVENTION

The present invention relates to compounds having the formula

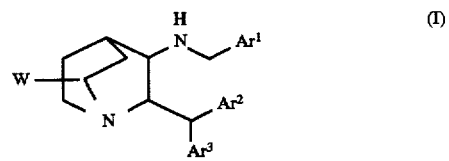

wherein W is Y or $X(CH_2)_n$;

Y is optionally substituted $(C_1-C_6)$alkyl, optionally substituted $(C_1-C_6)$alkenyl or optionally substituted $(C_3-C_8)$cycloalkyl;

X is optionally substituted $(C_1-C_6)$alkoxy, hydroxy, $CONR^1R^2$, $CO_2R^1$, $CHR^1OR^2$, $CHR^1NR^2R^3$, $COR^1$, $CONR^1OR^2$ or optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and n is an integer from zero to six;

$Ar^1$, $Ar^2$ and $Ar^3$ are each, independently, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl;

and $R^1$, $R^2$ and $R^3$ are independently selected from hydrogen, optionally substituted $(C_1-C_6)$alkyl, optionally substituted $(C_1-C_6)$alkoxy, optionally substituted $(C_3-C_8)$cycloalkyl, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and optionally substituted $(C_1-C_5)$ heterocyclic groups, wherein said heterocyclic groups are selected from pyrrolidino, piperidino, morpholino, piperazinyl and thiamorpholino; and when X is $CONR^1R^2$, $R^1$ and $R^2$ may form, together with the nitrogen to which they are attached, a morpholino or thiamorpholino group;

and wherein the substituents on the foregoing substituted alkyl, alkenyl, cycloalkyl and alkoxy groups are independently selected from halo, nitro, amino, $(C_1-C_4)$alkyl, $(C_1-C_4)$alkoxy, trifluoromethyl and trifluoromethoxy;

and wherein the substituents on the foregoing substituted $(C_1-C_5)$ heterocyclic groups are attached to a sulfur or nitrogen atom on the ring and are independently selected from oxygen, di-oxygen and $(C_1-C_4)$alkyl when attached to a ring sulfur atom, and are independently selected from oxygen and $(C_1-C_4)$alkyl when attached to a ring nitrogen atom;

and wherein the substituents on said substituted $Ar^1$ groups are independently selected from $(C_1-C_6)$alkyl optionally substituted with from one to three halo groups, ($C_1$–$C_6$)alkoxy optionally substituted with from one to three halo groups, ($C_1$–$C_6$) alkylsulfinyl, ($C_2$–$C_6$)alkenyl, ($C_1$–$C_6$) alkylthio, ($C_1$–$C_6$)alkylsulfonyl, ($C_1$–$C_6$) alkylsulfonylamino, and di-($C_1$–$C_6$)alkylamino wherein one or both of the alkyl groups may be optionally substituted with a ($C_1$–$C_6$)alkylsulfonyl, or ($C_1$–$C_6$)alkylsulfinyl group;

and wherein the substituents on said substituted $Ar^2$ and $Ar^3$ groups are independently selected from ($C_1$–$C_4$)alkyl, ($C_1$–$C_4$)alkoxy, ($C_1$–$C_4$)alkylthio, ($C_1$–$C_4$)alkylsulfinyl, di-($C_1$–$C_4$)alkylamino, trifluoromethyl and trifluoromethoxy;

with the proviso that: (a) Y can not be (i) unsubstituted straight or branched ($C_1$–$C_6$)alkyl, (ii) unsubstituted straight or branched ($C_2$–$C_6$)alkenyl, (iii) straight or branched ($C_1$–$C_6$)alkyl substituted with ($C_1$–$C_4$)alkyl, or (iv) straight or branched ($C_2$–$C_6$)alkenyl substituted with ($C_1$–$C_4$)alkyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The term "alkyl" is used herein to mean straight or branched hydrocarbon chain radicals including, but not limited to, methyl, ethyl, n-propyl, isopropyl, n-butyl, isobutyl, t-butyl, and the like.

The term "alkenyl" is used herein to mean straight or branched hydrocarbon chain radicals having one double bond including, but not limited to, ethenyl, 1- and 2-propenyl, 2-methyl-1-propenyl, 1- and 2-butenyl and the like.

The term "alkoxy" is used herein to mean —OR (R is alkyl) including, but not limited to, methoxy, ethoxy, propoxy, isopropoxy, n-butoxy, isobutoxy, t-butoxy and the like.

The term "alkylthio" is used herein to mean —SR (R is alkyl) including, but not limited to, methylthio, ethylthio, n-propylthio, isopropylthio, n-butylthio, isobutylthio, t-butylthio and the like.

The term "cycloalkyl" is used herein to mean cyclic hydrocarbon radicals including, but not limited to, cyclopropyl, cyclobutyl, cyclopentyl, cyclohexyl and the like.

The term "halo" is used herein to mean chloro, fluoro, bromo or iodo.

Preferred compounds of the present invention are those wherein Y is —COOH, $Ar^2$ and $Ar^3$ are diphenylmethyl and $Ar^1$ is a disubstituted phenyl group.

Specific preferred compounds of this invention include the following:

(3R,4S,5S,6S)-5-(5-isopropyl-2-methoxybenzylamino)-6-diphenylmethyl-1-azabicyclo[2.2.2]octane-3-carboxylic acid;

(3R,4S,5S,6S)-5-(2-methoxy-5-methylthiobenzylamino)-6-diphenylmethyl-1-azabicyclo[2.2.2]octane-3-carboxylic acid;

(3R,4S,5S,6S)-5-(2,5-dimethoxybenzylamino)-6-diphenylmethyl-1-azabicyclo[2.2.2]octane-3-carboxylic acid;

(3R,4S,5S,6S)-5-(2-methoxy-5-methylbenzylamino)-6-diphenylmethyl-1-azabicyclo[2.2.2]octane-3-carboxylic acid;

(3R,4S,5S,6S)-5-(5-ethyl-2-methoxybenzylamino)-6-diphenylmethyl-1-azabicyclo[2.2.2]octane-3-carboxylic acid;

(3R,4S,5S,6S)-5-(2-methoxyl-5-n-propylbenzylamino)-6-diphenylmethyl-1-azabicyclo[2.2.2]octane-3-carboxylic acid;

(3R,4S,5S,6S)-5-(5-sec-butyl-2-methoxybenzylamino)-6-diphenylmethyl-1-azabicyclo[2.2.2]octane-3-carboxylic acid;

(3R,4S,5S,6S)-5-(5-N-methyl-methanesulfonylamino-2-methoxybenzylamino)-6-diphenylmethyl-1-azabicyclo[2.2.2]octane-3-carboxylic acid;

(3R,4S,5S,6S)-5-(2-methoxy-5-methylsulfinylbenzylamino)-6-diphenylmethyl-1-azabicyclo[2.2.2]octane-3-carboxylic acid;

(3R,4S,5S,6S)-5-(2-methoxy-5-trifluoromethoxybenzylamino)-6-diphenylmethyl-1-azabicyclo[2.2.2]octane-3-carboxylic acid;

(3R,4S,5S,6S)-5-(2-methoxy-5-methylsulfonylbenzylamino)-6-diphenylmethyl-1-azabicyclo[2.2.2]octane-3-carboxylic acid;

(3R,4S,5S,6S)-5-(5-dimethylamino-2-methoxybenzylamino)-6-diphenylmethyl-1-azabicyclo[2.2.2]octane-3-carboxylic acid;

(2S,4S,5S,6S)-5-(5-isopropyl-2-methoxybenzylamino)-6-diphenylmethyl-1-azabicyclo[2.2.2]octane-2-carboxylic acid;

(2S,4S,5S,6S)-5-(2-methoxy-5-methylthiobenzylamino)-6-diphenylmethyl-1-azabicyclo[2.2.2]octane-2-carboxylic acid;

(2S,4S,5S,6S)-5-(2,5-dimethoxybenzylamino)-6-diphenylmethyl-1-azabicyclo[2.2.2]octane-2-carboxylic acid;

(2S,4S,5S,6S)-5-(2-methoxy-5-methylbenzylamino)-6-diphenylmethyl-1-azabicyclo[2.2.2]octane-2-carboxylic acid;

(2S,4S,5S,6S)-5-(5-ethyl-2-methoxybenzylamino)-6-diphenylmethyl-1-azabicyclo[2.2.2]octane-2-carboxylic acid;

(2S,4S,5S,6S)-5-(2-methoxyl-5-n-propylbenzylamino)-6-diphenylmethyl-1-azabicyclo[2.2.2]octane-2-carboxylic acid;

(2S,4S,5S,6S)-5-(5-sec-butyl-2-methoxybenzylamino)-6-diphenylmethyl-1-azabicyclo[2.2.2]octane-2-carboxylic acid;

(2S,4S,5S,6S)-5-(5-N-methyl-methanesulfonylamino-2-methoxybenzylamino)-6-diphenylmethyl-1-azabicyclo[2.2.2]octane-2-carboxylic acid;

(2S,4S,5S,6S)-5-(2-methoxy-5-methylsulfinylbenzylamino)-6-diphenylmethyl-1-azabicyclo[2.2.2]octane-2-carboxylic acid;

(2S,4S,5S,6S)-5-(2-methoxy-5-trifluoromethoxybenzylamino)-6-diphenylmethyl-1-azabicyclo[2.2.2]octane-2-carboxylic acid;

(2S,4S,5S,6S)-5-(2-methoxy-5-methylsulfonylbenzylamino)-6-diphenylmethyl-1-azabicyclo[2.2.2]octane-2-carboxylic acid; and (2S,4S,5S,6S)-5-(5-dimethylamino-2-methoxybenzylamino)-6-diphenylmethyl-1-azabicyclo[2.2.2]octane-2-carboxylic acid.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as engine, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

Formula I above includes compounds identical to those depicted but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like. Included among the radiolabelled forms of compounds of the formulae I and VII are the tritium and $C^{14}$ isotopes thereof.

DETAILED DESCRIPTION OF THE INVENTION

The novel compounds of the present invention can be prepared as described in the following reaction schemes and discussions. Unless otherwise indicated, W, $Ar^1$, $Ar^2$, $Ar^3$, X, Y, $R^1$, $R^2$, $R^3$ and n in the reaction schemes and discussion that follow are defined as above.

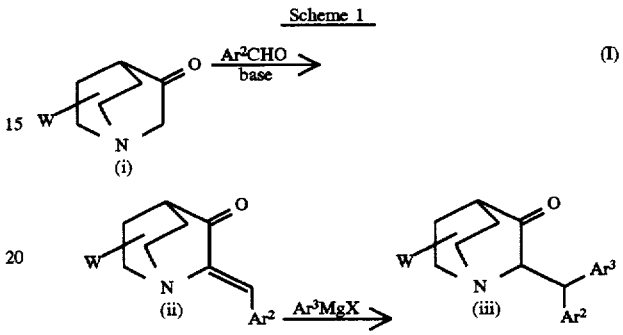

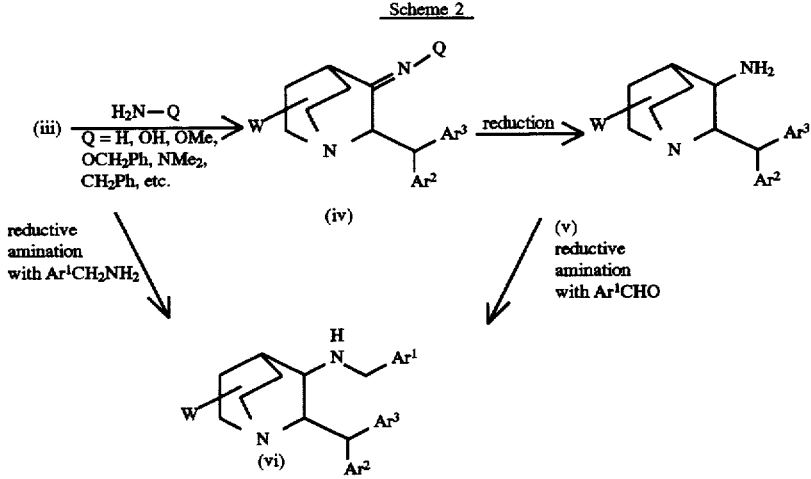

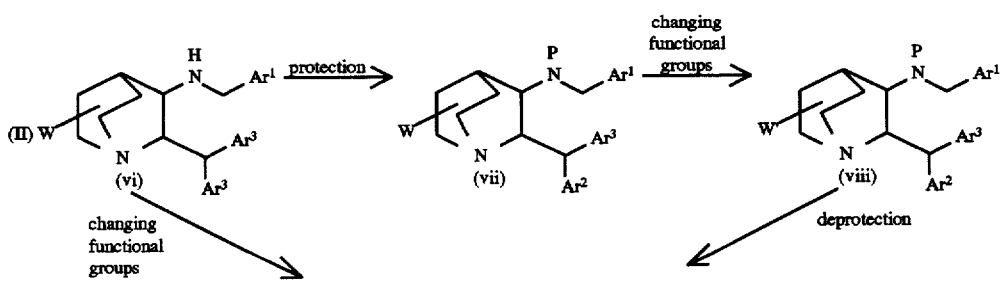

-continued
Scheme 3

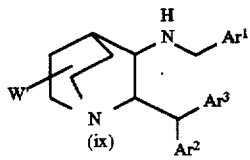

(ix)

The compounds of the formula I may be prepared by a number of synthetic methods. In the above schemes, $Ar^1$, $Ar^2$ and $Ar^3$ are as previously defined, each of W and W' represents the substituent —$(CH_2)_nX$ or Y, defined as for formula I above, or an equivalent of $(CH_2)_nX$ or Y in the synthetic process. P and Q represent, respectively, appropriate nitrogen protecting groups.

Substituted quinuclidine-3-ones (i) can be prepared from properly substituted isonicotinates by the method for preparing unsubstituted quinuclidine-3-ones reported in Org. Synth. Coll. Vol. V, 989 (1973). For example, 5-methyl-, 5-methoxycarbonyl- and 5-diethyl-aminocarbonyl-quinuclidin-3-ones have already been prepared by this method (J. Chem. Soc. Perkin Trans., 1, 409 (1991)).

Introduction of a benzhydryl group or its congener at the 2 position of a quinuclidine-3-one (i) can be accomplished using the procedure reported in J. Med. Chem., 18, 587 (1975). Compound (i) can be converted to the 2-benzyliden compound (ii) by aldol condensation with an aromatic aldehyde ($Ar^2CHO$) catalyzed by a base such as sodium hydroxide in a protic solvent (e.g., ethanol). This reaction is preferably conducted at the reflux temperature of the solvent.

Introduction of another aryl group ($Ar^3$) can be accomplished via a Grignard reaction in an aprotic solvent such as tetrahydrofuran (THF), ether or toluene. The addition of catalytical amount of copper(I) halide such as cuprous bromide or iodide improves the yield of the 1,4-addition product. This reaction is usually conducted at low temperatures such as from $-78°$ to $0°$ C. In some cases, the procedure reported by Kuwajima (Tetrahedron, 45, 349 (1989)) employing trimethylsilylchloride, hexamethylphosphoramide (HMPA) and cuprous bromide dimethylsulfide complex (CuBr-DMS) is preferred to improve the selectivity. The resulting compound (iii), if desired, can be converted to the corresponding carboxylic acid by acid catalyzed hydrolysis. The carboxylic acid can be converted, if desired, to corresponding amide by methods well known to those skilled in the art.

Compound (iii) can be converted to the claimed compounds (vi) by two independent routes. The first route involves direct introduction of an arylmethylamino group ($Ar^1CH_2NH$—) at the 3 position of the quinuclidine ring. This transformation is accomplished by, first, formation of an imine with (iii) and a corresponding benzylamine. This reaction is usually catalyzed by an acid (e.g., camphor sulfonic acid (CSA)), and conducted in hot toluene under dehydrolytic conditions. Then, the imine is reduced to afford compound (vi). This reduction can be carried out by catalytic hydrogenation, or with several hydride reagents such as aluminum-based reagents, boranes, borohydrides or trialkylsilanes. In most cases, the reaction with trialkylboranes (e.g., 9-borabicyclo[3.3.1]nonane (9-BBN)) or sodium triacetoxyborohydride ($NaBH(OAc)_3$) in THF at room temperature for a half hour to a few days gives satisfactory results.

The second route involves stepwise syntheses via the 3-amino of compound (v), which is then alkylated to afford (vi). Compound (iv) is an imino-type derivative such as an oxime, hydrazone or imine. It can be formed by reaction of (iii) with the corresponding $Q-NH_2$ (e.g., a hydroxylamine, N,N-dimethylhydrazone, ammonia or benzylamine). The obtained product (iv) can be reduced using any one of a variety of reducing reagents. Appropriate reducing agents include lithium aluminum hydride (LAH), borane reagents, catalytic hydrogenation or a combination of the foregoing. In the case of imines derived from ammonia, formic acid can be used as a reductant. The formed 3-amino derivative (v) is then arylmethylated with a proper benzaldehyde ($Ar^1CHO$) under ordinary conditions for reductive amination, e.g., sodium cyanoborohydride in methanol (J. Am. Chem. Soc., 93, 2897 (1971)). Several other reducing agents such as sodium borohydride ($NaBH_4$), sodium triacetoxyborohydride ($NaBH(OAc)_3$) or trialkylsilanes can be also used to perform this transformation.

The functional group W in compound (vi) can be changed to another functionality W'. Some of the claimed compounds (ix) can be obtained in this manner. For example, a compound (vi) wherein W is an amide can be converted into the corresponding amine derivative by reacting it with an appropriate reducing reagent such as LAH. It can also be converted into the corresponding carboxylic acid by hydrolysis.

The carboxylic acid so obtained can be converted into a corresponding ester by a standard procedures that are known to those skilled in the art.

Compounds (vi) wherein W is an ester or a carboxylic acid can be converted to the corresponding hydroxymethyl by treating with a suitable reducing agent such as LAH.

The above described conversions from one functional group W to another W' are standard procedures that will be obvious to those skilled in the art.

If the benzylamine interferes with such transformation, appropriate protection of NH group of the benzylamine of (vi) is necessary. For such protection, Cbz or Boc group is suitable (c.f. T. W. Greene, Protective Groups in Organic Synthesis, J. Wiley & Sons (1981)). After finishing transformation of the functional group, the protecting group is removed by a suitable standard procedure to provide the claimed compound (ix).

Inasmuch as the quinuclidine compounds of this invention all possess at least one asymmetric center, they are capable of occurring in various stereoisomeric forms or configurations. Hence, the compounds can exist in separated (+)- and (−)-optically active forms, as well as in racemic or (±)-mixtures thereof, and in the case of those compounds with two asymmetric centers, they can additionally exist as diastereomers with respective optical isomers thereof. The present invention is meant to include all such forms within its scope. For instance, the diastereomers can be separated by methods well known to those skilled in the art, e.g., by fractional crystallization and the like, while the optically-active isomers can be obtained by simply resolving the chemistry that are known for these purposes.

Insofar as the majority of 3-arylmethylamino-2-benzhydryl quinuclidine compounds of this invention are basic compounds, they are all capable of forming a wide variety of different salts with various inorganic and organic acids. Although such salts must be pharmaceutically acceptable for administration to animals, it is often desirable in practice to initially isolate the quinuclidine base compound from the reaction mixture as a pharmaceutically unacceptable salt and then simply convert to the free base compound by treatment with an alkaline reagent and thereafter, subsequently convert the free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent or a suitable organic solvent such as methanol or ethanol. Upon careful evaporation of the solvent, the desired solid salt is readily obtained.

The acid which are used to prepare the pharmaceutically acceptable acid addition salts of the aforementioned quinuclidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, gluconate, saccharate, benzoate, methanesulfonate, benzenesulfonate, p-toluenesulfonate and pamoate (i.e., 1,1'-methylene-bis-(2-hydroxy-3-naphthoate))salts.

Some quinuclidine compounds of the invention which have also acidic groups are capable of forming base salts with various pharmacologically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic quinuclidine derivatives. These particular non-toxic base salts include those derived form such pharmacologically acceptable cations as sodium, potassium, calcium and magnesium, etc. These salts can easily be prepared by treating the aforementioned acidic quinuclidine compounds with an aqueous solution containing the desired pharmacologically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The compounds of formula I and their pharmaceutically acceptable salts (hereinafter referred to, collectively, as "the active compounds of this invention") exhibit significant substance P receptor-binding activity and therefore, are of value in the treatment of a wide variety of clinical conditions which are characterized by the presence of an excess of said substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, as well as pain in any of the aforesaid conditions, including migraine. Hence, these compounds are readily adapted to therapeutic use as substance P antagonists for the control and/or treatment of any of the aforesaid clinical conditions in mammals, including humans.

The active compounds of this invention can be administered via either the oral, parenteral or topical routes. In general, these compounds are most desirably administered in doses ranging from about 2.8 mg. up to 1500 mg per day, although variations will necessarily occur depending upon the weight and condition of the subject being treated and the particular route of administration chosen. However, a dosage level that is in the range of form about 0.07 mg to about 21 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The active compounds of this invention may be administered alone or in combination with pharmaceutically acceptable carriers or diluents by any one of the three routes previously indicated, and such administration can be carried out in single or multiple doses. More particularly, the active compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH ) 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention may be determined by their ability to inhibit the binding of substance P at its receptor sites in bovine caudate tissue or IM-9 cells employing radioactive ligands. The substance P antagonist activity of the herein described quinuclidine compounds is evaluated by using the standard assay procedure described by M. A. Cascieri et al., as reported in the Journal of Biological Chemistry, Vol.258, p.5158 (1983). This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. In this test, some preferred compounds indicated $IC_{50}$ values, in the range of 0.1–60 nM, with respect to inhibition of binding at its receptor.

The anti-inflammatory activity of the compounds of the present invention may be determined using the standard carrageenin-induced rat foot edema test (described by C. A. Winter et al., Proceedings of the society of Experimental Biology and Medicine, Vol.111, P.544 (1962)). In this test, anti-inflammatory activity is determined as the percent inhibition of edema formation in the hind paw of male albino rats (weighing 150–190 g) in response to a sub-plantar injection of carrageenin. The carrageenin is injected as a 1% aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving thr vehicle alone is significant on comparison with the results afforded by a standard compound like phenylbutazone at 33 mg/kg, via the oral route of administration.

The anti-psychotic activity of the compounds of the present invention as neuroleptic agents for the control of various psychotic disorders may be determined primarily by a study of their ability to suppress substance P-induced hypermotility in rats. This study is carried out by first dosing the rats with a control compound or with an appropriate test compound of the present invention, then injecting the rats with substance P by intracerebral administration via canula and thereafter measuring their individual locomotor response to said stimuli.

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad.

In the reaction schemes and procedures that appear in the examples, Me represents methyl, Et represents ethyl, Ph represents phenyl, TFA represents trifluoroacetic acid, and t-Boc represents t-butoxycarbonyl.

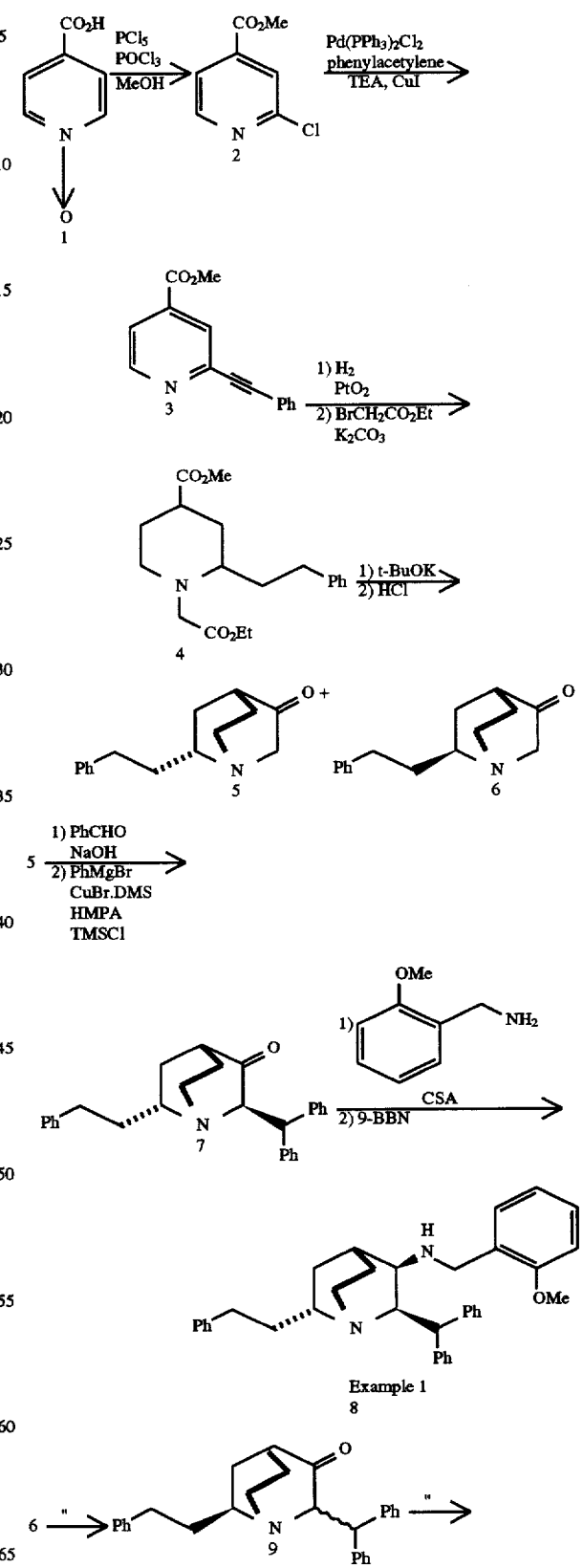

EXAMPLES
SYNTHETIC SCHEME FOR EXAMPLES 1–3

EXAMPLES
SYNTHETIC SCHEME FOR EXAMPLES 1-3

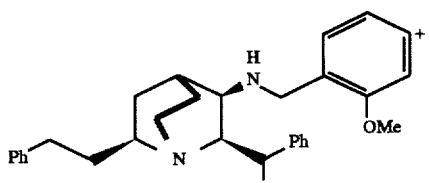

Example 2
10

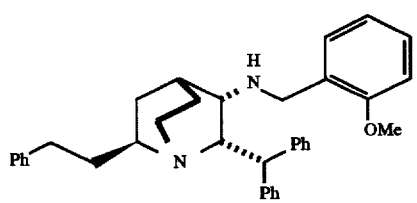

Example 3
11

EXAMPLE 1

A. Methyl 2-chloroisonicotinate (2)

Isonicotinic acid N-oxide, 1 (50.0 g, 0.359 mol), phosphorous pentachloride (120 g, 0.576 mol) and phosphorous oxychloride (160 ml, 1.72 mol) were mixed together with stirring at room temperature. The mixture was heated at reflux for 2 hours. The excess $POCl_3$ was removed by distillation at 1 Torr and then by evaporation under vacuum. The residue was carefully quenched with dried methanol to give an exothermic reaction. The mixture was basified with aq. $NaHCO_3$, and extracted with EtOAc. The extracts were dried over $MgSO_4$, and concentrated down by evaporation. The crude products were distilled under vacuum to afford methyl 2-chloroisonicotinate, 2 (136°–144° C./36 mm Hg, 41.6 g). Although this material contained an impurity (c.a. 18% mol determined by $^1$H NMR), it did not affect the next reaction.

$^1$H NMR ($CDCl_3$): 8.54 (br.d, J=5 Hz, 1H), 7.89 (br.s, 1H), 7.77 (dd, J=5, 1 Hz, 1H), 3.97 (s, 3H).

B. Methyl 2-(2-phenylethynyl)isonicotinate (3)

Methyl 2-chloroisonicotinate, 2 (19.08 g, 0.111 mol as 100% pure), phenylacetylene (13.6 g, 0.133 mol), cuprous iodide (1.00 g, 5.25 mmol) and triethylamine (30 ml) were mixed together with stirring at room temperature, and to this mixture was added bis(triphenylphosphine) palladium (II) chloride (2.0 g, 2.85 mmol). The reaction mixture was heated at reflux for 7 hours. The solvent was removed by evaporation, and the residue was subjected to chromatography (silica-gel, 10–30% EtOAc-hexane) followed by crystallization from ether/hexane to afford methyl 2-(2-phenylethynyl) isonicotinate, (11.25 g, 43%).

$^1$H NMR ($CDCl_3$): 8.77 (br d, J=5 Hz, 1H), 8.08 (m, 1H), 7.78 (dd, J=5, 2 Hz, 1H), 7.62 (m, 2H), 7.38 (m, 3H), 3.98 (s, 3H).

C. Methyl (N-ethoxycarbonylmethyl-2-phenethyl-piperidin)-4-carboxylate (4)

The isonicotinate, 3 (12.75 g, 53.8 mmol) was dissolved in acetic acid (18 ml), and was catalytically hydrogenated with $PtO_2$ (459 mg) at 50 kg/cm$^2$ for 15 hours using an autoclave. The catalyst was removed by filtration through Celite, and washed with toluene. The filtrate was concentrated to provide a mixture of the cis/trans piperidine isomers (16.36 g, c.a. 5:1). The above crude products and ethylbromoacetate (10.8 g, 64.7 mmol) were dissolved in toluene (150 ml), and $K_2CO_3$ (15 g, 109 mmol) was suspended to the resultant solution. The mixture was heated at reflux for 5 hours, and, the reaction was quenched with aq. $NH_4Cl$. The resultant mixture was extracted with EtOAc, washed with brine, and dried over $Na_2SO_4$. Evaporation of the solvent afforded a mixture of cis/trans isomers of 4 (18.91 g).

$^1$H NMR ($CDCl_3$), 4-cis isomer (less polar, major): 7.31–7.16 (m, 5H), 4.14 (q, J=7 Hz, 2H), 3.69 (s, 3H), 3.47 (d, J=17 Hz, 1H), 3.39 (d, J=17 Hz, 1H), 3.00 (m, 1H), 2.77–2.53 (m, 4H), 2.38 (tt, J=12.4 Hz, 1H), 2.03 (m, 1H), 1.96–1.64 (m, 3H), 1.52 (q, J=12 Hz, 2H), 1.25 (t, J=7 Hz, 3H) 4-trans isomer (more polar, minor): 3.36 (d, J=17 Hz, 1H), 3.29 (d, J=17 Hz, 1H).

D. 6-Phenethylquinuclidin-3-one (5) & (6)

To a mixture of potassium t-butoxide and toluene (50 ml) heated at reflux was gradually added the crude mixture of 4 dissolved in toluene (100 ml). Addition required for 3 hours, and the resultant mixture was heated for additional 1 hour. The reaction was quenched with 6N-HCl, and the solvent was removed by evaporation. To the residue was added 12N-HCl (40 ml), and the mixture was heated at 120° C. overnight. Concentration of the reaction mixture formed undesired solids, which were removed by filtration. The filtrate was basified with NaOH and $NaHCO_3$ to pH=8.5, and extracted with EtOAc. The extracts were washed with brine, and dried over $Na_2SO_4$. Evaporation of the solvent yielded the diastereomeric mixture of 5 and 6 (8.36 g). An analysis on $^1$H NMR of this material showed the presence of c.a. 2:1 mixture of 5 (α-phenethyl; more polar) and 6 (β-isomer; less polar). The mixture of 5 and 6 was subjected to chromatography (silica-gel, 50%–70% EtOAc-hexane) to afford a fraction enriched with 5 (0.68 g, ca. 8:1), one with 6 (0.58 g, ca. 1:10) and unseparated fractions (5.24 g).

Data of a compound 5.

$^1$H NMR (270 MHz, $CDCl_3$): 7.32–7.17 (m, 5H), 3.47 (d, J=19 Hz, 1H), 3.11 (d, J=19 Hz, 1H), 3.05–2.80 (m, 3H), 2.69 (m, 2H), 2.42 (m, 1H), 2.18 (m, 1H), 1.96 (m, 2H), 1.89–1.49 (m, 3H).

$^{13}$C NMR ($CDCl_3$): 219.0, 141.4, 127.86, 127.93, 125.3, 56.1, 53.7, 48.6, 40.2, 36.2, 32.0, 31.9, 24.6.

Data of a compound 6

$^1$H NMR (270 MHz, $CDCl_3$): 7.32–7.14 (m, 5H), 3.38 (d, J=18 Hz, 1H), 3.23 (d, J=18 Hz, 1H), 2.86–2.65 (m, 4H), 2.40 (m, 1H), 2.17 (m, 1H), 2.05–1.76 (m, 4H), 1.54 (m, 1H).

$^{13}$C NMR ($CDCl_3$): 219.1, 141.4, 127.8, 125.3, 63.8, 54.8, 40.1, 39.4, 36.2, 32.5, 32.4, 25.1.

E. (2R*,4R*,6R*)-2-Diphenylmethyl-6-phenethylquinuclidin-3-one (7)

Compound 5 (577 mg, 2.52 mmol), benzaldehyde (328 mg, 3.09 mmol) and NaOH (7.6 mg, 0.19 mmol) were dissolved in EtOH (8 ml), and the resultant solution was heated at reflux for 1 day. After the solvent was removed by evaporation, the residue was diluted with ether/$NH_4Cl$ aq. The organic layer was washed with brine, and dried over $Na_2SO_4$. After evaporation of the solvent the residual oil was purified by chromatography (silica-gel, 5–20% EtOAc/ hexane) to afford the 2-benzylidene compound of 5 (738 mg, 92%). To a cold suspension of CuBr/dimethylsulfide (27 mg, 0.13 mmol) in toluene (6 ml) at −60° C. was added phenylmagnesium bromide (3.0M in ether, 1.25 ml). To this reagent was added a mixture of the above 2-benzylidene compound (738 mg, 2.33 mmol), chlorotrimethylsilane (0.71 ml, 5.6 mmol), HMPA (0.98 ml, 5.6 mmol) and toluene (6 ml) keeping the inner temperature below −60° C. After 1 hour, the reaction mixture was gradually warmed up to 0° C. The reaction was quenched with AcOH (0.43 ml) at −60° C., and to this was added ether and water. The solution was adjusted at pH=4, and the organic layer was washed with brine, and dried over $Na_2SO_4$. The solvent was removed by evaporation, and the crude material was purified by chromatography (silica-gel, 13–50%, EtOAc/hexane) to afford pure 7 (357 mg, 39%).

$^1$H NMR (270 MHz, CDCl$_3$): 7.42–7.10 (m, 15H), 4.44 (d, J=9.2 Hz, 1H), 4.18 (d, J=9.2 Hz, 1H), 2.95–2.78 (m, 2H), 2.69–2.47 (m, 3H), 2.39 (m, 1H), 2.15–0.52 (m, 6H).
$^{13}$C NMR (CDCl$_3$): 220.1, 143.1, 142.6, 141.7, 128.3, 128.2, 128.14, 128.07, 126.1, 125.6, 65.2, 56.1, 50.0, 44.0, 41.9, 35.6, 32.3, 31.6, 27.1.

F. (2R*,3R*,4R*,6R*)-2-Diphenylmethyl-3-(2-methoxybenzylamino)-6-phenethyl-1-azabicyclo [2.2.2]octane (8)

Compound 7 (357 mg, 0.904 mmol), 2-methoxybenzylamine (189 mg, 1.38 mmol) and camphorsulfonic acid (2.0 mg) were dissolved in toluene (30 ml), and the resultant mixture was heated at reflux for 3 days under a dehydrating condition with MS 4A. After replacement of the solvent with THF a solution of 9-BBN (0.5M in THF, 5.4 ml) was added, and the resultant mixture was stirred for 4 days at room temperature. After evaporation of the solvent the residue was basified at pH=13, extracted with $CH_2Cl_2$, dried over $Na_2SO_4$, and concentrated down. The crude material was purified by combination of column chromatography (silica-gel, MeOH/$CH_2Cl_2$), preparative TLC (silica-gel, 10% MeOH/$CH_2Cl_2$) and crystallization from MeOH to provide pure compound 8 (109 mg, 23%).

M.p.: 107.1°–107.9° C.

IR (nujol): 1493, 1243 cm$^{-1}$.

$^1$H NMR (CDCl$_3$): 7.35–6.95 (m, 16H), 6.78–6.67 (m, 2H), 6.58 (dd, J=7.3, 1.5 Hz, 1H), 4.52 (d, J=12 Hz, 1H), 3.63 (dd, J=12, 8 Hz, 1H), 3.58 (d, J=13 Hz, 1H), 3.53 (s, 3H), 3.38 (m, 1H), 3.27 (d, J=13 Hz, 1H), 2.81 (dd, J=8, 4.4 Hz, 1H), 2.59–2.47 (m, 2H), 2.06 (m, 1H), 1.96 (m, 2H), 1.85 (m, 1H), 1.74 (m, 1H), 1.62–1.37 (m, 2H), 1.21 (m, 1H), 0.99 (m, 1H).

EXAMPLES 2 AND 3

(2R*,3R*,4R*,6S*)- and (2R*,3R*,4S*,6R*)-2-Diphenyl methyl-3-(2-methoxybenzylamino)-6-phenethyl-1-azabicyclo[2.2.2]octane (10) & (11)

Compound 6 was converted to a mixture of 10 and 11 through 9 by the same method for 8 from 5.

9-exo isomer (less polar)

$^1$H NMR (270 MHz, CDCl$_3$): 4.44 (d, J=9.2 Hz, 1H), 3.83 (d, J=9.2 Hz, 1H)

$^{13}$C NMR (CDCl$_3$): 219.9, 74.2, 57.3, 50.8, 41.8, 35.7, 34.3, 33.4, 32.7, 26.0.

9-endo isomer (more polar)

$^1$H NMR (270 MHz, CDCl$_3$): 4.52 (d, J=7.5 Hz, 1H), 4.04 (d, J=7.5 Hz, 1H).

$^{13}$C NMR (CDCl$_3$): 220.6, 72.6, 50.3, 49.2, 41.6, 41.4, 35.5, 32.3, 24.8.

(2R*,3R*,4R*,6S*)-2-Diphenylmethyl-3-(2-methoxybenzyl)amino-6-phenethyl-1-azabicyclo [2.2.2]octane M.p.: 110.0°–114.7° C.

IR (nujol): 1599, 1587, 1232 cm$^{-1}$.

$^1$H NMR (CDCl$_3$): 7.35–7.06 (m, 14H), 6.77–6.67 (m, 4H), 6.59 (dd, J=7.4, 1.6 Hz, 1H), 4.61 (d, J=12 Hz, 1H), 3.59 (d, J=13 Hz, 1H), 3.53 (s, 3H), 3.42 (m, 1H), 3.27 (d, J=13 Hz, 1H), 3.14 (m, 1H), 2.86 (dd, J=8, 4 Hz, 1H), 2.68 (m, 1H), 2.50 (m, 1H), 2.42–2.20 (m, 2H), 2.04 (m, 1H), 1.88 (m, 2H), 1.63–1.42 (m, 2H), 1.25–1.09 (m, 2H).

(2R*,3R*,4S*,6R*)-2-Diphenylmethyl-3-(2-methoxybenzyl)amino-6-phenethyl-1-azabicyclo [2.2.2]octane M.p.: 122.4°–125.3° C.

IR (nujol): 1494, 1243, 1052 cm$^{-1}$.

$^1$H NMR (CDCl$_3$): 7.37–7.00 (m, 16H), 6.77 (t, J=7.4 Hz, 1H), 6.71 (d, J=7.9 Hz, 1H), 3.59 (d, J=14 Hz, 1H), 3.55 (s, 3H), 3.32 (d, J=14 Hz, 1H), 3.32–3.26 (m, 1H), 2.91–2.80 (m, 2H), 2.48 (m, 1H), 2.33 (t, J=8.4 Hz, 2H), 2.07 (m, 2H), 1.60–1.41 (m, 4H), 0.82 (m, 1H).

EXAMPLE 4

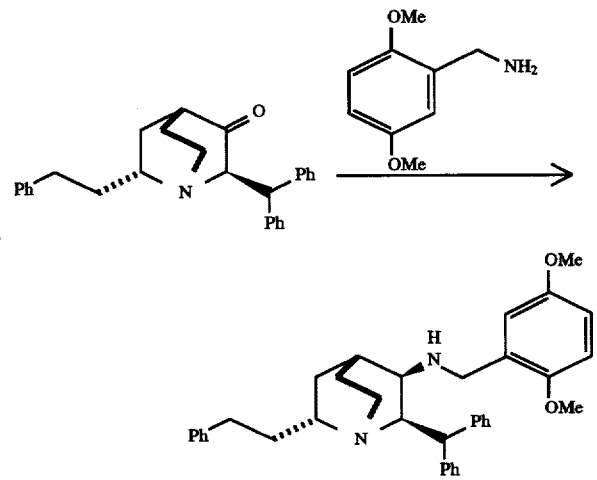

(2R*,3R*,4R*,6R*)-2-Diphenylmethyl-3-(2,5-dimethoxybenzyl)amino-6-phenethyl-1-azabicyclo [2.2.2]octane A compound of Example 4 were prepared from compound 7 and 2,5-dimethoxybenzylamine by the same procedure for Example 1.

M.p.: 123.5°–124.8° C.

IR (nujol): 1499, 1492, 1226 cm$^{-1}$.

$^1$H NMR (CDCl$_3$): 7.35–6.95 (m, 16H), 6.67 (dd, J=9.3 Hz, 1H), 6.60 (d, J=9 Hz, 1H), 6.37 (d, J=3 Hz, 1H), 4.52 (d, J=13 Hz, 1H), 3.73 (s, 3H), 3.63 (m, 1H), 3.53 (d, J=13 Hz, 1H), 3.49 (s, 3H), 3.37 (m, 1H), 3.18 (d, J=13 Hz, 1H), 2.84 (dd, J=7.5, 4.3, 1H), 2.60–2.44 (m, 2H), 2.10–1.68 (m, 5H), 1.50 (m, 2H), 1.20 (m, 1H), 1.01 (m, 1H).

EXAMPLES 5-8
SYNTHETIC SCHEME FOR EXAMPLES 5-8

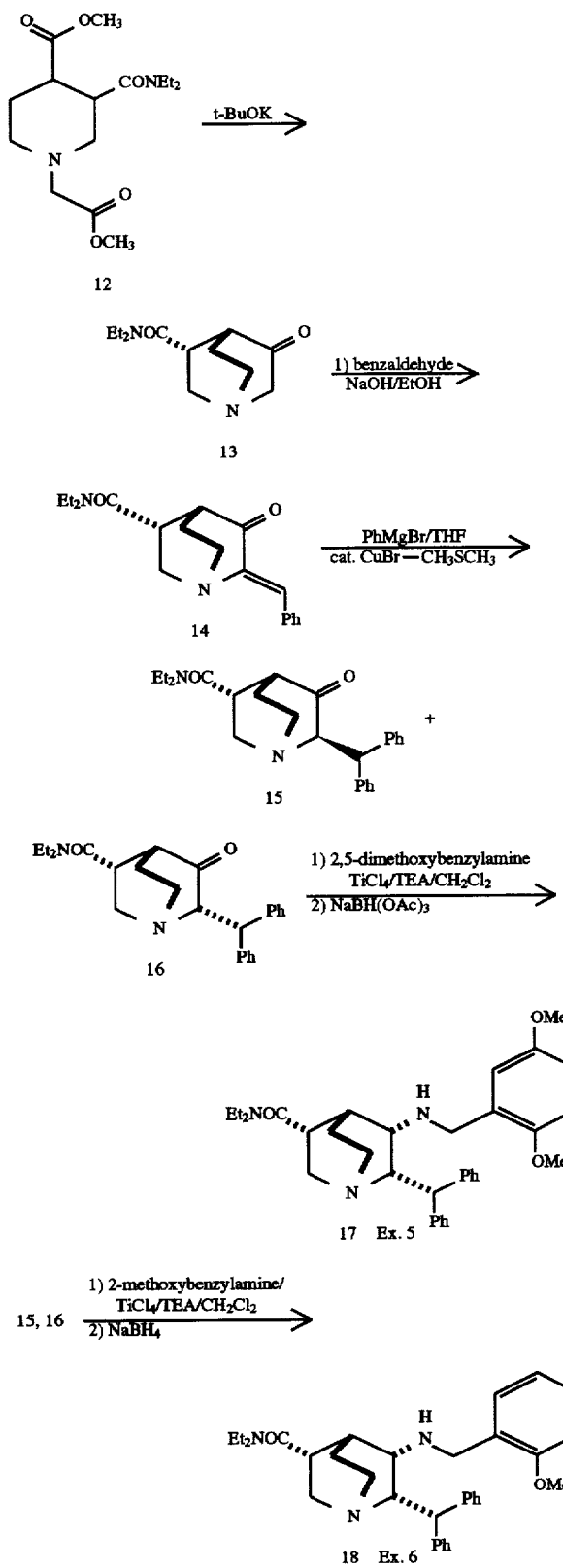

-continued
EXAMPLES 5-8
SYNTHETIC SCHEME FOR EXAMPLES 5-8

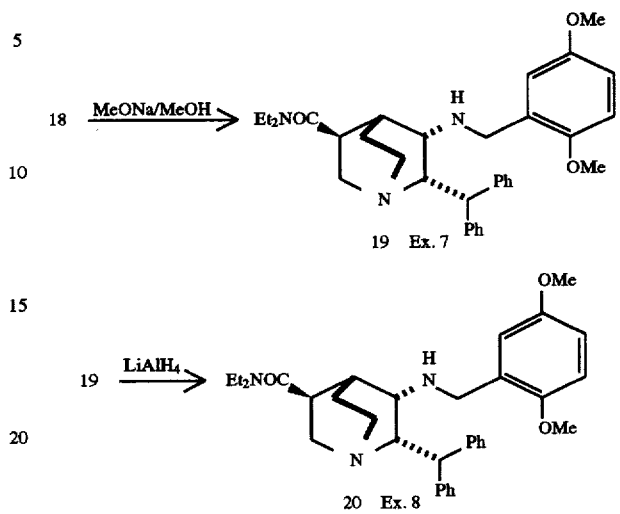

EXAMPLE 5

(3R*,4R*,5S*,6S*)-N,N-Diethyl-5-(2,5-dimethoxybenzylamino)-6-diphenylmethyl-1-azabicyclo[2.2.2]octane-3-carboxamide (17)

A. cis-Methyl-3-(Diethylcarbamoyl)-1-(methoxycarbonylmethyl)-piperidine-4-carboxylate (12)

cis-Methyl-3-(Diethylcarbamoyl)-1-(methoxycarbonylmethyl)piperidine-4-carboxylate, 12 was prepared according to the procedure reported in Tetrahedron Letters, 1989, 30, P.5795–5798 and J. Chem. Soc., PERKIN TRANS. 1., 1991, P.409–420.

B. (3R*,4R*)-N,N-Diethyl-5-oxo-1-azabicyclo[2.2.2]octane-3-carboxamide (13)

A solution of 12 (159 g, 0.503 mole) in toluene (700 ml) was added dropwise over a period 2.5 hours to a solution of potassium t-butoxide (169 g, 1.51 mole) in toluene (1.9 L) at 110° C. under a nitrogen condition. The mixture was heated at reflux for 1 hour and cooled down to room temperature. Water (400 ml) was added then the layers were heated at reflux for 2 hours. After the organic layer was separated, the aqueous layer was neutralized and extracted with EtOAc for 15 hours with continuous extraction apparatus. The combined extracts were dried over $MgSO_4$ and concentrated down. Recrystallization from EtOH gave 13 (34.6 g, 31%) as a colorless crystal. The stereochemistry was determined by X-Ray analysis, $^{13}C$ and NMR.

IR (KBr): 2975, 2915, 2875, 1726, 1629, 1483, 1462, 1454, 1434, 1410, 1382, 1368, 1296, 1253, 1141, 1081, 1052 $cm^{-1}$.

$^1H$ NMR ($CDCl_3$): 3.6 (d, J=8 Hz, 1H), 3.5–3.1 (m, 8H), 3.0–2.9 (m, 2H), 2.5 (dd, J=6, 3 Hz, 1H) 2.2 (dd, J=8.3 Hz, 2H), 1.2 (t, J=7 Hz, 3H), 1.1 (t, J=8 Hz, 3H).

$^{13}C$ NMR ($CDCl_3$) 215.4, 173.2, 62.5, 51.5, 45.9, 42.3, 42.0, 41.3, 40.5, 25.9, 15.0, 12.9.

C. (3R*,4R*)-N,N-Diethyl-5-oxo-6-benzylidene-1-azabicyclo[2.2.2]octane-3-carboxamide (14)

A mixture of 13 (34.6 g, 154 mmole), benzaldehyde (17.4 g, 164 mmole) and NaOH (6.5 g, 164 mmole) in EtOH (400 ml) was refluxed for 3 hours. After cooling the reaction mixture to room temperature, the resulting yellow crystal was collected by filtration and washed with cold EtOH and dried in vacuo to give 14 (38.4 g, 128 mmole). The filtrate was concentrated under reduced pressure to give a second crop (3.3 g, 11 mmole) (total 41.7 g, 139 mmole, 90%).

IR (KBr): 2960, 2930, 2875, 1706, 1640, 1453, 1445, 1427, 1315, 1260, 1136, 1094, 694 $cm^{-1}$.

$^1$H NMR (CDCl$_3$): 8.0 (dd, J=8.6 Hz, 2H), 7.3 (m, 3H), 7.1 (s, 1H), 3.4–3.0 (m, 6H), 2.7 (dd, J=5.0, 3.0 Hz, 2H), 1.2 (t, J=7 Hz, 3H), 1.1 (t, J=8 Hz, 3H).

$^{13}$C NMR (CDCl$_3$): 202.5, 172.9, 143.8, 134.1, 132.0, 129.3, 128.2, 125.2, 52.3, 47.7, 46.4, 43.5, 42.0, 41.9, 40.5, 25.9, 15.1, 13.1.

D. (3R*,4R*,6R*)-N,N-Diethyl-5-oxo-6-diphenylmethyl-1-azabicyclo[2.2.2]octane-3-carboxamide and (3R*,4R*,6S*)-N,N-Diethyl-5-oxo-6-diphenylmethyl-1-azabicyclo[2.2.2]octane-3-carboxamide (15) & (16)

A 1 L four necked flask, equipped with a mechanical stirrer and a thermometer was flame dried and furnished with a nitrogen atmosphere. CuBr/CH$_3$SCH$_3$ (3.1 g, 15 mmole) was placed in this flask, dry THF (400 ml) was added and cooled to −50° C. To this suspension was added a 3M (an ether solution) phenylmagnesium bromide (50 ml, 150 mmole) dropwise over a period 20 minutes and stirred for 30 minutes at −60° C. A solution of 14 (45 g, 150 mmole) in 400 ml of dry THF (slightly heated to dissolve) was added into this reaction suspension under a nitrogen atmosphere dropwise over a period 1 hour. After the addition, the reaction mixture was stirred at 0° C. for 1.5 hours. Sat. NH$_4$Cl aq (100 ml) was added to the reaction mixture and the organic layer was washed with sat. NH$_4$Cl aq until the blue color disappeared. The blue water layers were extracted with EtOAc (100 ml×2). The combined organic layers were washed with brine, dried over MgSO$_4$, and concentrated down. The crude solid was purified by silica-gel chromatography (Hexane:EtOAc=1:1–1:2 as an eluent) to give 1,2 adduct (1.2 g, 3.1 mmole, 2%) and 1,4 adduct 15 and 16 (54 g, 138 mmole, 92%). The products ratio of 15/16 was changed by quenching temperature.

$^1$H NMR (CDCl$_3$) 15 isomer: 7.43 (d, J=7 Hz, 2H), 7.3–7.1 (m, 8H), 4.7 (d, J=7 Hz, 1H), 4.4 (d, J=7 Hz, 1H), 3.4–3.1 (m, 7H), 2.5–2.4 (m, 3H), 1.9–1.8 (m, 2H), 1.2 (t, J=3 Hz, 3H), 1.1 (t, J=7.3 Hz, 3H).

16 isomer: 7.4–7.2 (m, 10H), 4.8 (d, J=11 Hz, 1H), 3.96 (d, J=11 Hz, 1H), 3.6–3.5 (m, 1H), 3.4–2.8 (m, 8H), 2.5–2.4 (m, 1H), 1.9–1.8 (m, 2H), 1.2–1.1 (m, 6H).

E. (3R*,4R*,5S*,6S*)-N,N-Diethyl-5-(2,5-dimethoxybenzylamino)-6-diphenylmethyl-1-azabicyclo[2.2.2]octane-3-carboxamide (17)

Titanium tetrachloride (3.99 ml of a 1M solution in CH$_2$Cl$_2$, 3.99 mmole) was added to a mixture of 2,5-dimethoxybenzylamine (1.31 g, 7.84 mmole), triethylamine (2.14 ml, 15.4 mmole) and the mixture of 15 and 16 (the ratio of 15:16=11:8, 3.0 g, 7.68 mmole) in dry CH$_2$Cl$_2$ (20 ml) under a nitrogen atmosphere at 0° C. and stirred for 4 days at room temperature. The reaction mixture was poured into 1N-NaOH aq solution (c.a. 10 ml) at 5° C., and extracted with CH$_2$Cl$_2$. After separation of organic layer, the water layer was extracted with CH$_2$Cl$_2$. The combined organic layers were dried over MgSO$_4$ and concentrate down to give 4.54 g of crude imine. The crude imine was used to the next step without further purification. A solution of crude imine in THF (15 ml) was added into a suspension of NaBH(OAc)$_3$ (4.9 g, 23 mmole) in a solution of acetic acid (13 ml) and THF (10 ml) at 10° C. After stirring at room temperature for 1 hour, the reaction mixture was poured into 1N-NaOH aq solution (30 ml) at 5° C. and extracted with CH$_2$Cl$_2$ (10 ml×3). The combined organic extracts were washed with brine, dried over MgSO$_4$ and concentrated down. The crude oil was purified with silica gel chromatography (CH$_2$Cl$_2$:EtOAc=2:1, CH$_2$Cl$_2$:MeOH= 100:0.5–100:3) to give 17 (1.44 g, 2.7 mmole, 35%).

M.p.: 143.7°–145.6° C.

IR (KBr): 2965, 2935, 2885, 1621, 1494, 1483, 1475, 1465, 1463, 1431, 1214 $cm^{-1}$.

$^1$H NMR (CDCl$_3$): 7.3–6.9 (m, 10H), 6.6 (br.s, 2H), 6.4 (br.s, 1H), 4.65 (d, J=11 Hz, 1H), 3.9–3.05 (m, 8H), 3.7 (s, 3H), 3.6 (s, 3H), 2.9–2.6 (m, 4H), 2.5–2.35 (m, 2H), 1.75–1.45 (m, 2H), 1.2 (t, J=7 Hz, 3H), 1.1 (t, J=7 Hz, 3H).

EXAMPLE 6

(3R*4R*,5S*,6S*)-N,N-Diethyl-5-(2-methoxybenzylamino)-6-diphenylmethyl-1-azabicyclo[2.2.2]octane-3-carboxamide (18)

The compound 18 was prepared according to the procedure as 17 (NaBH$_4$ was used to reduce the crude imine). The stereochemistry of 18 was determined by $^1$H NMR and H—H COSY NMR.

M.p.: 121.2°–122.6° C.

IR (KBr): 3325, 2980, 2940, 2890, 1616, 1491, 1460, 1452, 1440, 1431, 1269, 1244, 1103, 1046, 1032 $cm^{-1}$.

$^1$H NMR (CDCl$_3$): 7.3–7.0 (m, 11H), 6.7–6.6 (m, 2H), 6.3 (d, J=7 Hz, 1H), 4.6 (d, J=12 Hz, 1H), 3.9–3.1 (m, 8H), 3.6 (s, 3H), 2.8–2.65 (m, 4H), 2.5–2.3 (m, 2H), 1.8–1.4 (m, 2H), 1.2 (t, J=7 Hz, 3H), 1.1 (t, J=7 Hz, 3H).

EXAMPLE 7

(3R*,4S*,5R*,6R*)-N,N-Diethyl-5-(2,5-dimethoxybenzylamino)-6-diphenylmethyl-1-azabicyclo[2.2.2]octane-3-carboxamide (19)

A mixture of 17 (506 mg, 0.93 mmole) and 20%-MeONa/MeOH (140 ml) was heated at reflux under a nitrogen atmosphere for 3 hours. After cooling the reaction mixture, the resulting white suspension was poured into crushed ice and extracted with CH$_2$Cl$_2$ (80 ml×3). The combined organic layers were washed with brine, dried over MgSO$_4$, and concentrated down. The resulting crude solid was purified with silica-gel chromatography (CH$_2$Cl$_2$:MeOH=10:1) to give 19 (0.46 g, 0.8 mmole, 92%).

M.p.: 167.8°–168.2° C.

IR (KBr): 2980, 2940, 2800, 1632, 1503, 1463, 1451, 1431, 1268, 1048 $cm^{-1}$.

EXAMPLE 8

(2R*,3R*,4S*,5S*)-5-(N,N-Diethylaminomethyl)-3-(2,5-dimethoxybenzylamino)-2-diphenylmethyl-1-azabicyclo[2.2.2]octane (20)

A solution of 19 (300 mg, 0.65 mmole) in dry THF (2 ml) was added to a suspension of LiAlH$_4$ (105 mg, 2.75 mmole) in 5 ml of dry THF at 5° C. and stirred at room temperature for 1 hour. Na$_2$SO$_4$/10H$_2$O (2 g) was added to the reaction mixture and stirred for 15 hours at room temperature. The suspension was filtrated, and the solids were washed with dry THF. The filtrate was concentrated under reduced pressure. The resulting oil was dissolved in 2 ml of acetone, and CH₃SO₃H (159 mg, 1.65 mmole) was added to the solution of the crude oil in acetone (2 ml). The resulting precipitate was collected by filtration and dried in vacuo to give 20 (254 mg, 0.31 mmole, 57%).

M.p.: 239.7°–242.2° C. (dec.)

IR (KBr): 3455, 2980, 2950, 1504, 1466, 1227, 1203, 1196, 1059, 1051, 1044 cm⁻¹.

mixture was poured into cold aqueous sodium bicarbonate (NaHCO₃) (250 ml) and extracted with methylene chloride (CH₂Cl₂) (100 ml) three times. The combined extracts were dried over sodium sulfate (Na₂SO₄) and concentrated. The clude was purified by recrystallization from ethyl acetate (EtOAc)/hexane to give 21 (1:2 mixture at 6-position; 23 mmol, 88%).

¹H NMR (CDCl₃): 4.64 (d, J=12.1 Hz, Ph2C$\underline{H}$CH of one isomer), 4.33, 4.28 (d+d, J=12 Hz, a pair of Ph2C$\underline{H}$CH and Ph2CHC$\underline{H}$ of another isomer).

SYNTHETIC SCHEME FOR EXAMPLES 9-10

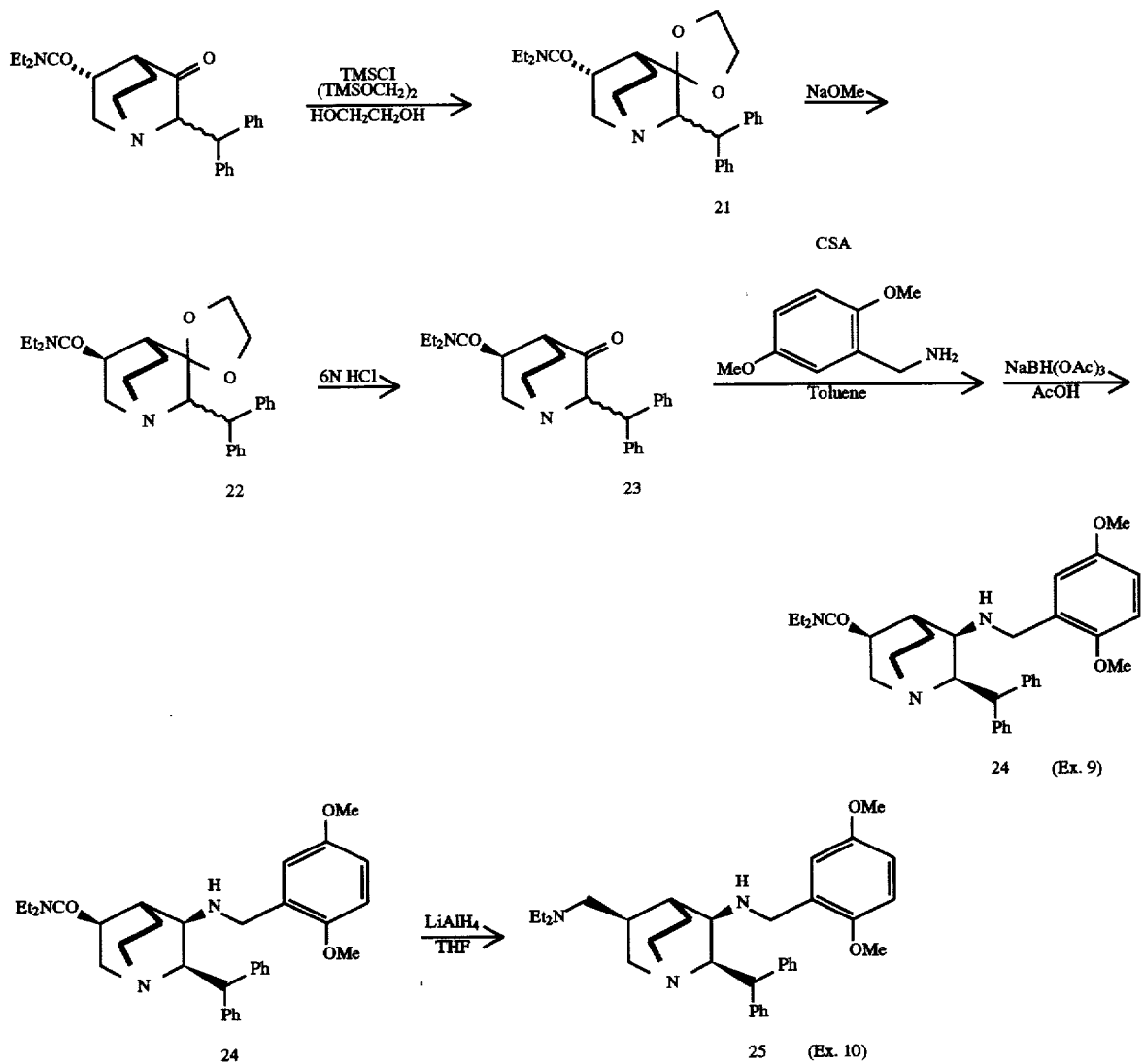

EXAMPLE 9

A. (3R*,4R*)-N,N-Diethyl-6-diphenylmethyl-5,5-ethylenedioxy-1-azabicyclo[2.2.2]octane-3-carboxamide (21)

A mixture of (3R*,4R*)-N,N-diethyl-6-diphenylmethyl-5-oxo-1-azabicyclo[2.2.2]octane-3-carboxamide (10 g, 26 mmol), 1,2-bis(trimethylsiloxy)ethane (6 g, 29 mmol), trimethylsilyl chloride (20 ml) and ethylene glycol (50 ml) was heated at 100° C. for 3 hours. After by-products were removed by distillation (93° C./atmosphere pressure), the MS(DI-EI): M/z=434 (M+).

B. (3R*,4S*)-N,N-Diethyl-6-diphenylmethyl-5,5-ethylenedioxy-1-azabicyclo[2.2.2]octane-3-carboxamide (22)

A suspension of 21 (9.8 g, 22 mmol) in sodium methoxide (28% in MeOH; 400 g) was heated at reflux temperature for 9 hours. The resulting solution was poured on ice (300 ml) and extracted with CH₂Cl₂ (150 ml) three times. The combined extracts were dried over sodium sulfate (Na₂SO₄) and concentrated. The clude was purified by recrystallization from ethanol (EtOH) to give 22 (1:4 mixture at 6-position; 8.4 g, 19 mmol, 87%).

¹H NMR (CDCl³): 4.40 (d, J=12.1 Hz, Ph2CHCH of one isomer), 4.34, 3.93 (d+d, J=12.5 Hz, a pair of Ph2CHCH and Ph2CHCH of another isomer).

MS(DI-EI): M/z=434 (M+).

C. (3R*,4S*)-N,N-Diethyl-6-diphenylmethyl-5-oxo-1-azabicyclo[2.2.2]octane-3-carboxamide (23)

A solution of 22 (6.5 g, 15 mmol) in 6N-HCl aq (100 ml) was heated at reflux for 10 hours. The resulting solution of sodium hydroxide (NaOH) (24 g) in water (100 ml) and extracted with CH₂Cl₂ (100 ml) four times. The combined extracts were dried over Na₂SO₄ and concentrated. The clude was purified by recrystallization from EtOH to give 23 (1:1 mixture at 6-position; 10 mmol, 68%).

¹H NMR (CDCl₃): 4.71, 3.95 (d+d, J=5.7 Hz, a pair of Ph2CCH and Ph2CHCH of one isomer), 4.47, 4.03 (d+d, J=8.4 Hz, a pair of Ph2CHCH and Ph2CHCH of another isomer).

D. (3R*,4S*,5S*,6S*)-N,N-Diethyl-5-(2,5-dimethoxybenzylamino)-6-diphenylmethyl-1-azabicyclo[2.2.2]octane-3-carboxamide (24)

A mixture of 23 (3.9 g, 10 mmol), 2,5-dimethoxybenzyl amine (1.9 g, 11 mmol) (*Acta. Chem. Scand.*, 25. p. 2629 (1971)) and camphor sulfonic acid (120 mg) in toluene (40 ml) was heated at reflux with removal of water for 8 hours and then the solvent was removed. The residue was dissolved in small amount of THF (c.a. 5 ml) and this solution was added to a solution of sodium triacetoxyborohydride (5.3 g, 25 mmol) in acetic acid (100 ml) at room temperature. The mixture was stirred at room temperature for 4 hours and the solvent was removed. Water (25 ml) was added and the mixture was neutralized with NaHCO₃ and extracted with EtOAc three times. The clude was purified by recrystallization from EtOAc to give 24 (2.4 g, 4.4 mmol, 44%).

M.p.: 153.1°–154.1° C.

IR (KBr): 1634, 1501, 1466, 1447, 1432, 1266, 1227 cm⁻¹.

¹H NMR (CDCl₃): 7.03–7.37 (m, 10H), 6.68 (dd, J=8.8, 2.5 Hz, 1H), 6.62 (d, J=8.8 Hz, 1H), 6.38 (d, J=2.5 Hz, 1H), 4.51 (d, J=12.1 Hz, 1H), 3.73 (s, 3H), 3.49 (s, 3H), 3.05–3.77 (m, 9H), 2.92 (dd, J=8.1, 4.4 Hz, 1H), 2.54–2.89 (m, 3H), 2.11 (br, 1H), 1.70–1.79 (m, 2H), 1.15 (t, J=7.3 Hz, 3H), 1.11 (t, J=7 Hz, 3H).

EXAMPLE 10

(2R*,3R*,4R*,5R*)-5-(N,N-Diethylaminomethyl)-3-(2,5-dimethoxybenzylamino)-2-diphenylmethyl-1-azabicyclo[2.2.2]octane (25)

To a suspension of lithium aluminum hydride (80 mg, 2.1 mmol) in THF (10 ml) was added 24 (220 mg, 0.41 mmol) at room temperature. The mixture was stirred at room temperature for 2 hours. Na₂SO₄/10H₂O (320 mg, 1 mmol) was added then the mixture was stirred for 10 minutes. After removal of the precipitate, the solution was concentrated. The residue was dissolved in hexane (20 ml) then filtered and concentrated to give 25 (210 mg, 0.39 mmol, 95%) as a colorless oil.

IR (KBr): 3430, 2935, 1499, 1467, 1459, 1450, 1226, 1050, 702 cm⁻¹.

¹H NMR (CDCl₃): 7.03–7.41 (m, 10H), 6.68 (dd, J=8.8, 3.0 Hz, 1H), 6.62 (d, J=8.8 Hz, 1H), 6.43 (d, J=2.8 Hz, 1H), 4.47 (d, J=12.1 Hz, 1H), 3.74 (s, 3H), 3.68 (dd, J=12.7, 7.9 Hz, 1H), 3.58 (d, J=13.2 Hz, 1H), 3.51 (s, 3H), 3.23 (d, J=13.2 Hz, 1H), 3.10–3.25 (m, 1H), 2.85–2.95 (m, 2H), 2.35–2.60 (m, 7H), 2.29 (dd, J=13.2, 2.5 Hz, 1H), 2.12 (br, 1H), 1.70–1.90 (m, 2H), 1.26–1.43 (m, 1H), 1.01 (t, J=7.1 Hz, 6H).

SYNTHETIC SCHEME FOR EXAMPLES 11 AND 12

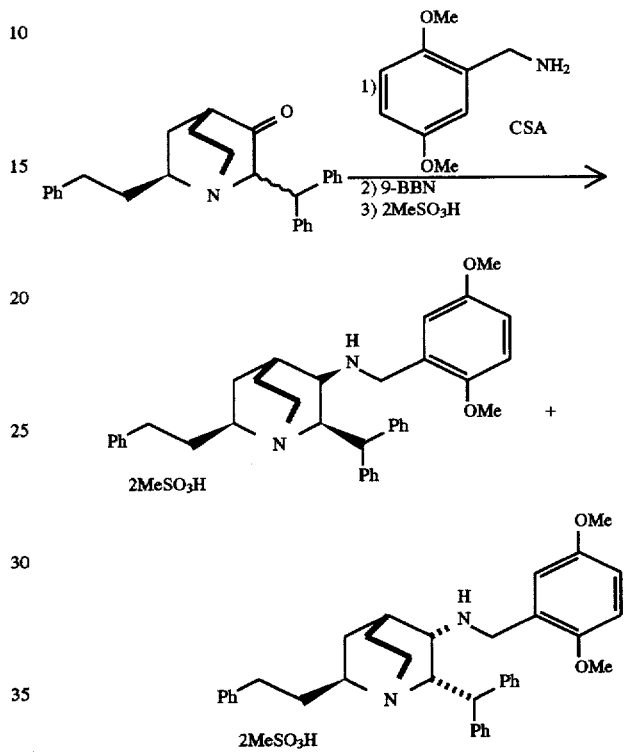

Example 11 and Example 12 were prepared by following a method for the synthesis of Example 2 and Example 3, and purified by sequential use of chromatography, preparative TLC and recrystallization of its dimesylate salt from acetone.

EXAMPLE 11

(2R*,3R*,4S*,6R*)-3-(2,5-Dimethoxybenzylamino)-2-diphenylmethyl-6-phenethyl-1-azabicyclo[2.2.2]octane dimesylate M.p.: 228.4°–232.3° C.

IR (nujol): 1154, 1039 cm⁻¹.

¹H NMR (CDCl₃): 7.37–7.01 (m, 15H), 6.69 (dd, J=8.9, 2.5 Hz, 1H), 6.63 (d, J=8.9 Hz, 1H), 6.42 (d, J=2.5 Hz, 1H), 4.50 (d, J=12.4 Hz, 1H), 3.74 (s, 3H), 3.70 (dd, J=12.4, 7.9 Hz, 1H), 3.57–3.52 (m, 1H), 3.52 (s, 3H), 3.31–3.21 (m, 1H), 3.23 (d, J=13 Hz, 1H), 2.91–2.80 (m, 2H), 2.48 (m, 1H), 2.32 (m, 2H), 2.12–1.97 (m, 2H), 1.69–1.30 (m, 4H), 0.81 (m, 1H).

EXAMPLE 12

(2R*,3R*,4R*,6S*)-3-(2,5-Dimethoxybenzylamino)-2-diphenylmethyl-6-phenethyl-1-azabicyclo[2.2.2]octane dimesylate M.p.: 207.5°–212.0° C.

IR (nujol): 1602, 1163, 1039 cm⁻¹.

¹H NMR (CDCl₃): 7.34–7.06 (m, 13H), 6.72–6.53 (m, 4H), 6.37 (d, J=2.8 Hz, 1H), 4.61 (d, J=11.8 Hz, 1H), 3.73 (s, 3H), 3.53 (d, J=13.2 Hz, 1H), 3.49 (s, 3H), 3.43 (m, 1H), 3.20 (d, J=13.2 Hz, 1H), 3.13 (m, 1H), 2.89 (m, 1H), 2.67 (m, 1H), 2.50–2.26 (m, 3H), 2.03 (br.s, 1H), 1.88 (m, 2H), 1.65–1.43 (m, 2H), 1.20–1.05 (m, 2H).

SYNTHETIC SCHEME FOR EXAMPLES 13 AND 14

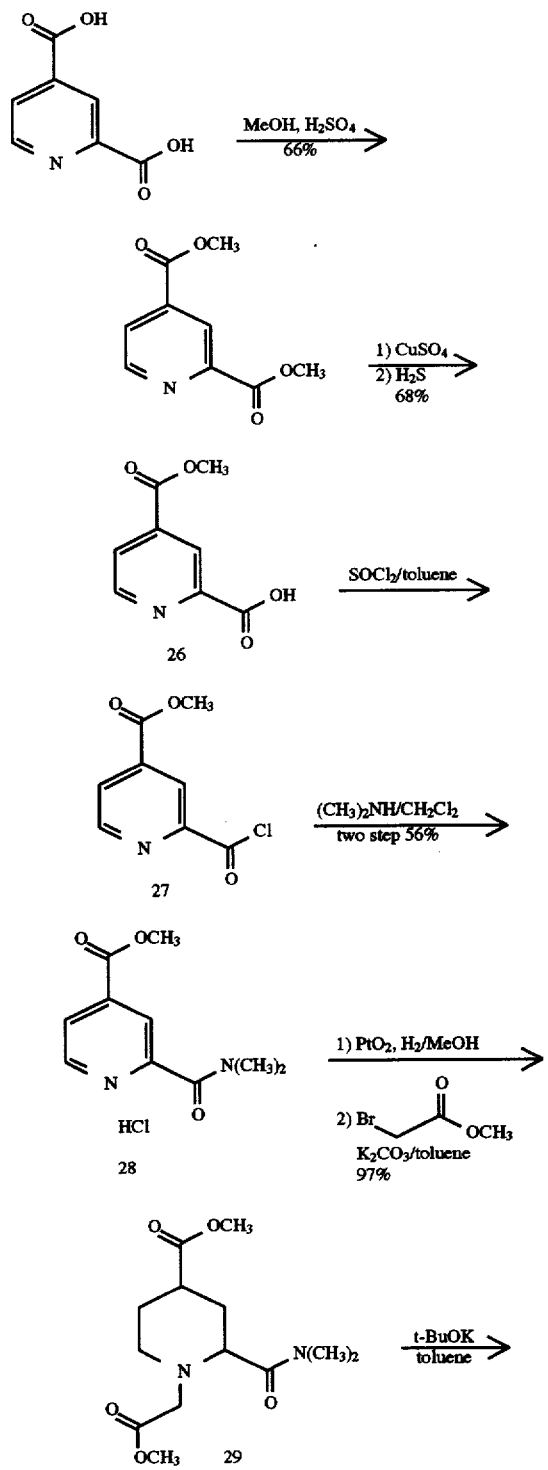

-continued
SYNTHETIC SCHEME FOR EXAMPLES 13 AND 14

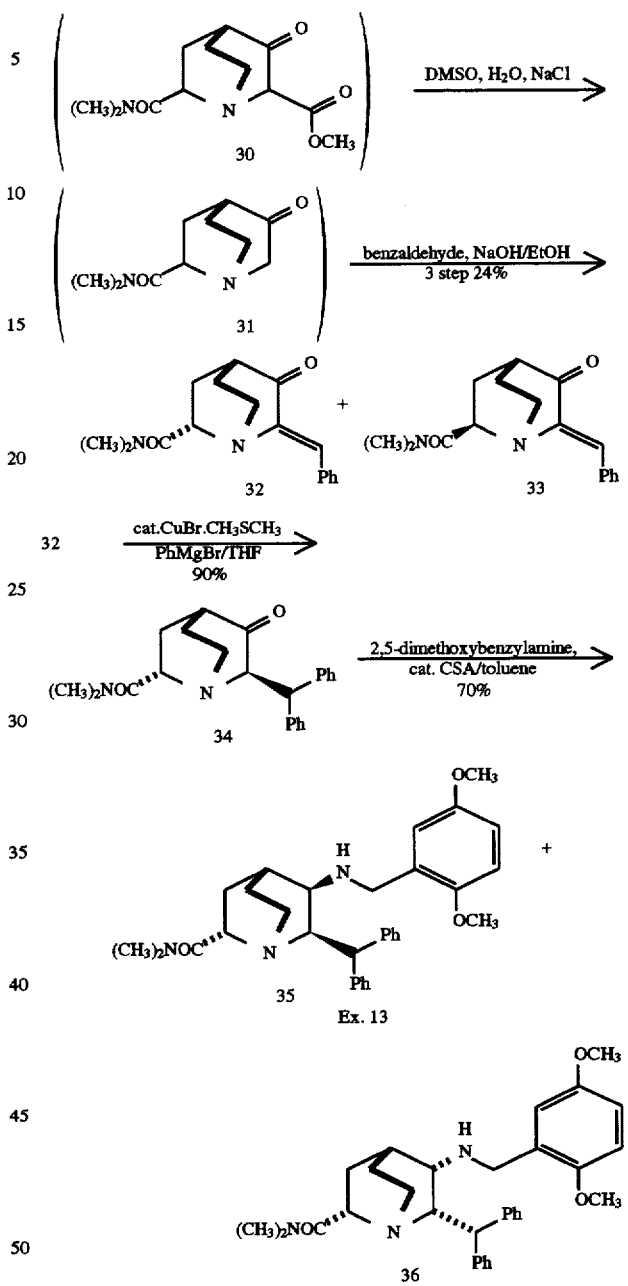

EXAMPLE 13

(2R*,4S*,5S*,6S*)-N,N-dimethyl-5-(2,5-dimethoxybenzyl)amino-6-diphenylmethyl-1-azabicyclo[2.2.2]octane-2-carboxamide (35)

A. 4-Methoxycarbonyl-pyridine-2-carboxylic acid (26)

The compound 26 was prepared according to the procedure reported in J. DE PHARMACIE DE BELGIQUE, 1969, 24, 3–21.

B. Methyl-2-dimethylcarbamoyl-pyridine-4-carboxylate (28)

A mixture of compound 26 (73 g, 0.4 mole), thionyl chloride (88 ml, 1.2 mole) in toluene (200 ml) was heated at reflux for 3 hours. The excess thionyl chloride was removed at an atmospheric pressure. Then toluene was removed under reduced pressure. The resulting light green acid chloride 27 was used without further purification. A solution of acid chloride 27 in $CH_2Cl_2$ (100 ml) was added to a suspension of dimethylamine hydrochloride (98.6 g, 1.2 mole) and triethylamine (1.3 mole) in $CH_2Cl_2$ (200 ml) at 0° C. dropwise over a period 10 minutes and stirred for 1 hour at room temperature. Water (200 ml) was added to the reaction mixture, water layer was extracted with $CH_2Cl_2$. The combined organic layers were washed with 1N NaOH, brine, dried over $MgSO_4$ and concentrated down. The crude solid was purified by silica gel short column chromatography (EtOAc as eluent) to give compound 28 (47 g, 226 mmole, 56%).

$^1$H NMR ($CDCl_3$): 8.74 (dd, J=5, 1 Hz, 1H), 8.19 (m, 1H), 7.90 (dd, J=5.2 Hz, 1H), 3.97 (s, 3H), 3.16 (s, 3H), 3.08 (s, 3H).

C. Methyl-2-dimethylcarbamoyl-1-(methoxycarbonylmethyl)piperidine-4-carboxylate (29)

A mixture of compound 28 (55.4 g, 0.27 mmole), conc. HCl (16 ml) in MeOH (62 ml) was hydrogenated over platinum oxide (1 g) at 8 kg/cm$^2$ for 24 hours. The catalyst was removed by filtration. The filtrate was concentrated under reduced pressure and the resulting oil was used without further purification. A mixture of crude intermediate compound hydrochloride, methyl bromoacetate (61 g, 0.4 mole) and $K_2CO_3$ (73.5 g, 0.53 mole) in toluene (200 ml) was heated at 70° C. for 3 hours. After cooling the reaction mixture, $H_2O$ (200 ml) was added and extracted with EtOAc (200 ml×2). The combined organic extracts were dried over $MgSO_4$ and concentrated down. The crude oil was purified by silica gel chromatography EtOAc as eluent to give 29 (69.8 g, 0.26 mole, 97%).

IR (neat) (cm$^{-1}$): 3455, 2955, 1735, 1726, 1648, 1636, 1498, 1435, 1249, 1205, 1198, 1169, 1138 1094.

D. (2R*,4S*)-2-benzyliden-6-dimethylcarbamoyl-3-oxo-1-azabicyclo[2.2.2]octane and (2R*,4R*)-2-benzyliden-6-dimethylcarbamoyl-3-oxo-1-azabicyclo-[2.2.2]octane (32) & (33)

A solution of 29 (30 g, 111 mmole) in toluene (150 ml) was added dropwise over a period 0.5 hour to a solution of potassium t-butoxide (37.4 g, 333 mmole) in toluene (400 ml) at 110° C. under a nitrogen condition. The mixture was heated at reflux for 0.5 hour and cooled down to room temperature. After evaporation of the solvent, water (200 ml) was added to the residue and the pH of the mixture was adjusted to pH=7 with concentrated HCl and concentrated down. The brown residue was purified by silica gel chromatography (EtOAc:MeOH=10:1 as eluent) to give brown oil (11.9 g). A mixture of the resulting crude oil, brine (1 ml) in DMSO (10 ml) was heated at 100° C. for 1.5 hours and concentrated under reduced pressure. A mixture of the residue, benzaldehyde (11.8 g, 111 mmole) and NaOH (4.44 g, 111 mmole) in EtOH (30 ml) was heated at reflux for 1.5 hours and concentrated down. Water was added to the reaction mixture and extracted with $CH_2Cl_2$ (50 ml×3). The combined organic extracts were dried over $MgSO_4$ and concentrated. The crude oil was purified by silica gel chromatography (EtOAc:Hexane=1:1 as eluent) to give compound 32 (7.65 g, 26.9 mmole, 24.2%) and 33 (200 mg, 0.7 mmole, 0.6%). Data of compound 32

$^1$H NMR ($CDCl_3$): 7.82–7.79 (m, 2H), 7.37–7.29 (m, 3H), 7.11 (s, 1H), 3.91 (dd, J=10, 6 Hz, 1H), 3.33–3.07 (m, 2H), 3.03 (s, 3H), 2.96–2.81 (m, 1H), 2.72–2.68 (m, 1H), 2.45 (s, 3H), 2.11–2.04 (m, 2H), 1.93–1.64 (m, 1H).

$^{13}$C NMR ($CDCl_3$): 204.2, 169.1, 141.1, 133.5, 131.4, 129.2, 127.8, 56.8, 47.8, 39.6, 36.8, 35.3, 25.8, 25.4.

Data of compound 33

$^1$H NMR ($CDCl_3$): 7.97–7.93 (m, 2H), 7.42–7.34 (m, 3H), 7.08 (s, 1H), 3.83–3.76 (m, 1H), 3.31–3.20 (m, 1H), 3.02–2.90 (m, 2H), 3.02 (s, 3H), 2.97 (s, 3H), 2.73–2.69 (m, 1H), 2.21–2.11 (m, 1H), 1.98–1.88 (m, 2H).

$^{13}$C NMR ($CDCl_3$): 205.3, 168.9, 143.7, 132.9, 131.6, 129.4, 128.0, 124.6, 56.4, 42.4, 40.1, 37.3, 35.8, 25.8, 25.0.

E. (2R*,4S*,6S*)-N,N-dimethyl-5-oxo-6-diphenylmethyl-1-azabicyclo[2,2,2]octane-2-carboxamide (34)

The compound 34 was prepared according to the same procedure as (3R*,4R*,6R*)-N,N-diethyl-5-oxo-6-diphenylmethyl-1-azabicyclo[2.2.2]octane-3-carboxamide (15).

IR (KBr): 1723, 1644 cm$^{-1}$.

$^1$H NMR ($CDCl_3$): 7.29–7.07 (m, 10H), 4.29 (d, J=10 Hz, 1H), 4.18 (d, J=10 Hz, 1H), 3.59 (m, 1H), 3.01–2.81 (m, 2H), 2.97 (s, 3H), 2.66–2.46 (m, 2H), 2.62 (s, 3H), 2.05–1.75 (m, 3H).

$^{13}$C NMR ($CDCl_3$): 218.5, 169.9, 143.6, 142.8, 128.2, 128.0, 127.8, 127.7, 126.1, 125.9, 66.8, 56.6, 49.8, 42.9, 41.1, 36.4, 36.1, 28.9, 24.2.

F. (2R*,4S*,5S*,6S*)-N,N-dimethyl-5-(2,5-dimethoxybenzyl)amino-6-diphenylmethyl-1-azabicyclo[2.2.2]octane-2-carboxamide (35)

A mixture of compound 34 (2.22 g, 6.13 mmole), 2,5-dimethoxybenzylamine (1.23 g, 7.36 mmole) and CSA (camphersulfonic acid) (20 mg) in toluene (50 ml) was heated at reflux for 24 hours with Dean Stark water separator. The solvent was removed under reduced pressure. The crude imine was used to the next step without purification. A solution of the crude imine in dry THF (20 ml) was added to a solution of NaBH(OAc)$_3$ (3.9 g, 18.4 mmole) and acetic acid (3 ml) in dry THF (20 ml) at 5° C. and stirred at room temperature for 15 hours. The pH value was adjusted to pH=10 by 1N NaOH, and extracted with EtOAc (20 ml×3). The combined organic extracts were washed with brine, dried over $MgSO_4$ and concentrated down. The crude oil was purified by silica gel chromatography (EtOAc:Hexane=1:1 as eluent) to give colorless oil. The oil was purified by recrystallization from MeOH to give compound 35 as colorless crystal (2.21 g, 4.3 mmole, 70%).

M.p.: 171.3°–174.5° C.

IR (KBr): 2940, 2875, 2835, 2800, 1644, 1504, 1463, 1450, 1307, 1225, 1049, 825, 705 cm$^{-1}$.

$^1$H NMR ($CDCl_3$): 7.29–7.00 (m, 10H), 6.67 (dd, J=9.3 Hz, 1H), 6.60 (d, J=9 Hz, 1H), 6.37 (d, J=3 Hz, 1H), 4.39 (d, J=12 Hz, 1H), 3.74 (s, 3H), 3.55–3.44 (m, 2H), 3.48 (s, 3H), 3.46–3.20 (m, 2H), 2.96 (dd, J=8.4 Hz, 1H), 2.72 (s, 3H), 2.59–2.51 (m, 1H), 2.43–2.35 (m, 1H), 2.21–2.11 (m, 1H), 2.11 (s, 3H), 1.97–1.89 (m, 1H), 1.59–1.49 (m, 1H), 1.29–1.18 (m, 1H).

EXAMPLE 14

(2R*,4S*,6R*,6R*)-N,N-dimethyl-5-(2,5-dimethoxybenzyl)amino-6-diphenylmethyl-1-azabicyclo[2.2.2]octane-2-carboxamide (36)

The title compound (36) was prepared by the procedure of Example 13. It was obtained from other fractions of the crude oil described in step F of Example 13 as a colorless oil and purified by recrystallization from MeOH as colorless crystal (244 mg, 0.5 mmole, 8%).

M.p.: 176.2°–178.9° C.

IR (KBr): 2945, 2860, 2835, 1635, 1597, 1493, 1459, 1281, 1220, 1053, 1027, 704 cm$^{-1}$.

$^1$H NMR (CDCl$_3$): 7.35–6.97 (m, 10H), 6.70–6.61 (m, 3H), 4.30 (d, J=13 Hz, 1H), 3.86–3.67 (m, 1H), 3.76 (s, 3H), 3.71 (s, 3H), 3.52 (d, J=14HZ, 1H), 3.32 (dd, J=11.5 Hz, 1H), 3.25 (d, J=14 Hz, 1H), 3.05–2.98 (m, 1H), 2.76–2.61 (m, 3H), 2.75 (s, 3H), 2.15 (s, 3H), 2.14 (br.s, 1H), 1.66–1.50 (m, 2H), 1.25–1.11 (m, 3H).

SYNTHETIC SCHEME FOR EXAMPLES 15–17

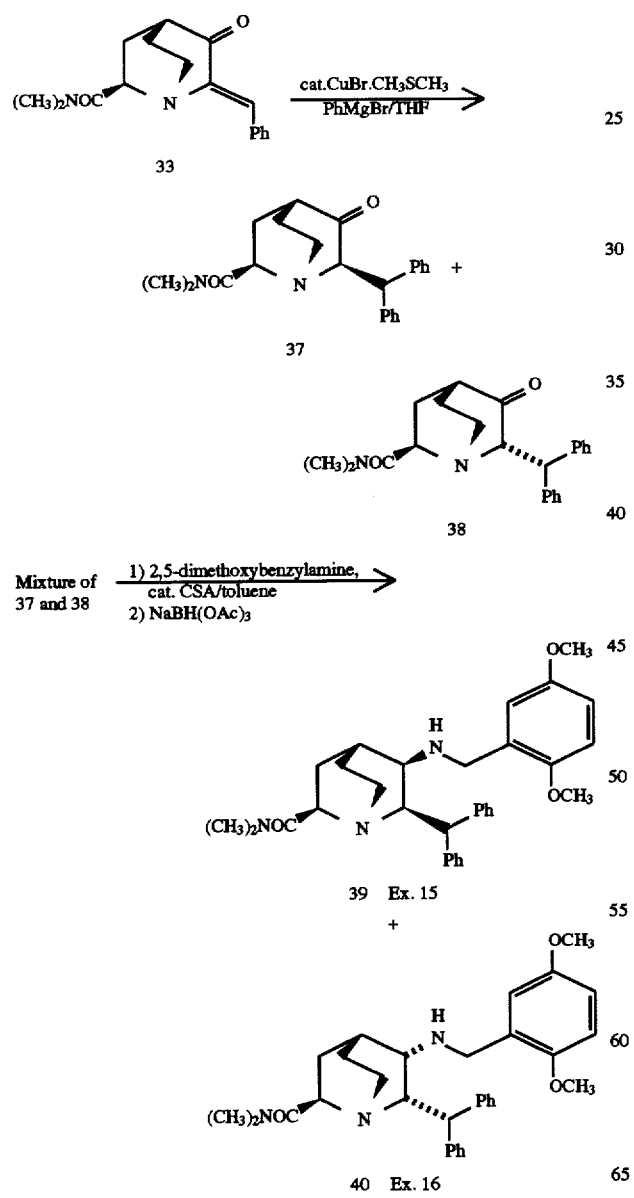

SYNTHETIC SCHEME FOR EXAMPLES 15–17
—continued

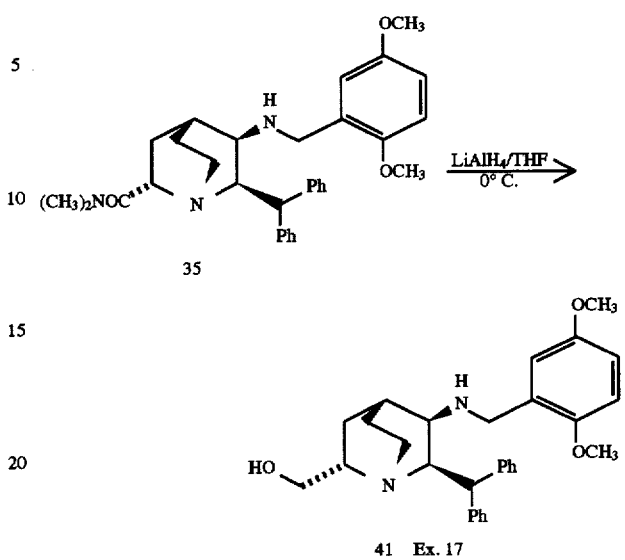

EXAMPLE 15

(2R*,4R*,5R*,6R*)-2-N,N-Dimethyl-5-(2,5-dimethoxybenzyl)amino-6-diphenylmethyl-1-azabicyclo[2.2.2]octane-2-carboxamide (39)

A. (2R*,4R*,6S*)-N,N-dimethyl-5-oxo-6-diphenylmethyl-1-azabicyclo-[2.2.2]octane-2-carboxamide and (2R*,4R*,6R*)-N,N-dimethyl-5-oxo-6-diphenylmethyl-1-azabicyclo-[2.2.2]octane-2-carboxamide (37 & 38)

The mixture of compounds 37 and 38 was prepared according to the same procedure as that described for the preparation of (3R*,4R*,6R*)-N,N-diethyl-5-oxo-6-diphenylmethyl-1-azabicyclo-[2,2,2]octane-3-carboxamide (15).

IR (KBr): 2935, 1733, 1726, 1634, 1493, 1452 cm$^{-1}$.

B. (2R*,4R*,5R*,6R*)-2-N,N-Dimethyl-5-(2,5-dimethoxybenzyl)amino-6-diphenylmethyl-1-azabicyclo[2.2.2]octane-2-carboxamide (39)

The title compound (39) was prepared in 22% yield and isolated as the dihydrochloride salt (2HCl).

M.p.: 224.6°–228.0° C. (dec.) (2HCl salt).

IR (KBr): 3435, 3175, 2960, 2925, 1663, 1575, 1510, 1235, 1040, 715 cm$^{-1}$ (2HCl salt).

$^1$H NMR (CDCl$_3$) (free form): 7.35–6.97 (m, 10H), 6.67 (dd, J=9.3 Hz, 1H), 6.60 (d, J=9 Hz, 1H), 6.39 (d, J=3 Hz, 1H), 4.52 (d, J=12 Hz, 1H), 3.72 (s, 3H), 3.57–3.50 (m, 2H), 3.46 (s, 3H), 3.35 (br.d, J=8, 4 Hz, 1H), 3.24 (d, J=13 Hz, 1H), 3.19–3.30 (m, 1H), 2.96 (dd, J=8, 4 Hz, 1H), 2.78 (s, 3H), 2.67–2.59 (m, 1H), 2.30–2.21 (m, 1H), 2.17 (s, 3H), 1.81–1.72 (m, 1H), 1.45–1.36 (m, 2H).

EXAMPLE 16

(2R*,4R*,5S*,6S*)-2-N,N-Dimethyl-5-(2,5-dimethoxybenzyl)amino-6-diphenylmethyl-1-azabicyclo[2.2.2]octane-2-carboxamide (40)

The title compound (40) was prepared in 7% yield by the procedure described above for the preparation of compound 39.

IR (neat) (free form): 2940, 1634, 1495, 1226 cm⁻¹.

¹H NMR (CDCl₃) (free form): 7.37–7.01 (m, 10H), 6.72–6.64 (m, 2H), 6.39 (d, J=2 Hz, 1H), 4.52 (d, J=12 Hz, 1H), 4.03 (br t, J=8 Hz, 1H), 3.90 (dd, J=12.7 Hz, 1H), 3.74 (s, 3H), 3.58 (s, 3H), 3.44 (d, J=8 Hz, 1H), 3.15 (d, J=8 Hz, 1H), 2.84–2.72 (m, 3H), 2.77 (s, 3H), 2.39 (s, 3H), 2.29–2.12 (m, 2H), 1.79–1.71 (m, 2H), 1.55–1.43 (m, 1H).

EXAMPLE 17

(2R*,3R*,4R*,6S*)-3-(2,5-Dimethoxybenzyl) amino-2-diphenylmethyl-6-hydroxymethyl-1-azabicyclo[2.2.2]octane (41)

Into a suspension of lithium aluminum hydride (LiAlH₄) (92 mg, 2.4 mmole) in dry THF (10 ml) at 0° C. was added a solution of compound 35 (417 mg, 0.8 mmole) in dry THF (10 ml) and heated at reflux for 1 hour. Na₂SO₄/10H₂O was added to the reaction mixture and stirred for 30 minutes. After cooling, the solids were removed by filtration and washed with THF. The filtrate was evaporated, added excess 10% HCl/MeOH and concentrated down. The resulting oil was purified by recrystallization from MeOH-Ether. The white crystal was collected by filtration and dried in vacuo to give compound 41 2HCl salt (240 mg, 0.44 mmole, 55%).

M.p.: 206.2°–207.9° C. (2HCl salt).

IR (KBr): 3490, 3430, 3210, 3130, 1505, 1450, 1229, 1047, 1040, 748, 710 cm⁻¹ (2HCl salt).

¹H NMR (CDCl₃) (free form): 7.33–7.05 (m, 10H), 6.67 (dd, J=9.3 Hz, 1H), 6.60 (d, J=9 Hz, 1H), 6.37 (d, J=3 Hz, 1H), 4.51 (d, J=12 Hz, 1H), 3.72 (s, 3H), 3.56–3.40 (m, 3H), 3.46 (s, 3H), 3.27–3.18 (m, 3H), 2.89–2.75 (m, 2H), 2.60–2.51 (m, 1H), 2.19–2.13 (m, 1H), 1.96–1.88 (m, 1H), 1.72–1.62 (m, 1H), 1.37–1.25 (m, 1H), 0.94–0.86 (m, 1H).

SYNTHETIC SCHEME FOR EXAMPLE 18

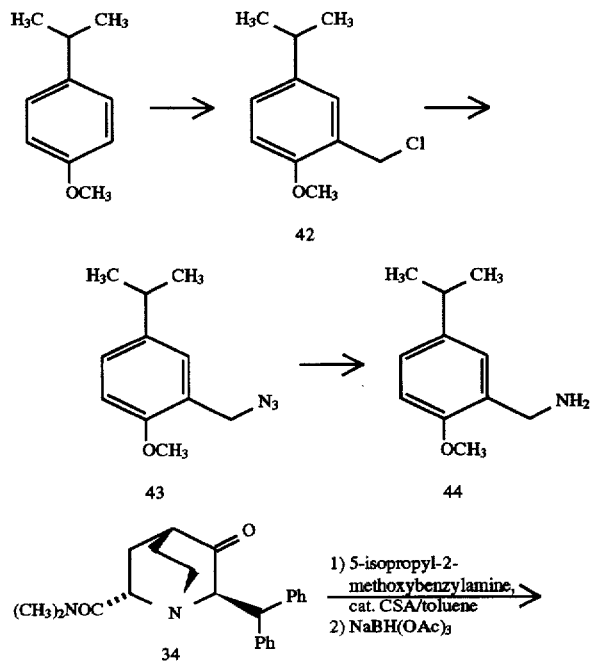

-continued
SYNTHETIC SCHEME FOR EXAMPLE 18

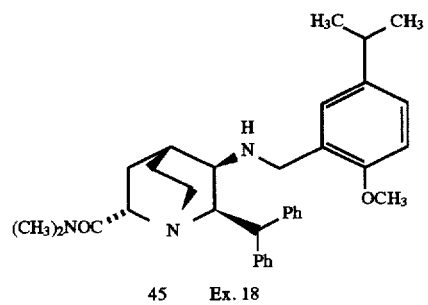

45   Ex. 18

EXAMPLE 18

(2R*,4S*,5S*,6S*)-N,N-dimethyl-5-(5-isopropyl-2-methoxybenzyl)-amino-6-diphenylmethyl-1-azabicyclo[2.2.2]octane-2-carboxamide (45)

A. 5-Isopropyl-2-methoxybenzyl amine (44)

5-Isopropyl-2-methoxybenzylchloride, 42 was prepared according to the same procedure reported in JP(kohyo) 501127/1983.

A mixture of resulting 42 (80 g, 0.37 mole) and sodium azide (NaN₃) (28.6 g, 0.44 mole) in dimethylformamide (DMF) (200 ml) was stirred at room temperature for 15 hours. The reaction mixture was poured into water and extracted with Et₂O. The combined Et₂O extracts were washed with water, brine and dried over magnesium sulfate (MgSO₄). After evaporation of the solvent, the resulting azide, 43 was used without further purification. The crude azide, 43 was hydrogenated over platinum dioxide (PtO₂) (1 g), under 2 kg/cm² for three days. The catalyst was removed by filtration with celite pad washed with MeOH. The combined filtrate was concentrated, the resulting crude amine was purified by distillation (bp 0.2 mm Hg, 93°–98° C.), to give colorless oil, 44 (21.6 g, 0.12 mole, 33%).

The data of compound 43 (azide)

IR (neat): 2105 cm⁻¹.

¹H NMR (270 MHz, CDCl₃): 7.18 (dd, J=8.2 Hz, 1H), 7.15 (d, J=2 Hz, 1H), 7.10 (d, J=8 Hz, 1H), 4.34 (s, 2H), 3.84 (s, 3H), 2.87 (hep, J=7 Hz, 1H), 1.22 (d, J=7 Hz, 6H).

The data of compound 44 (amine)

IR (neat): 2960, 1498, 1458, 1294, 1250, 1032 cm⁻¹.

¹H NMR (270 MHz, CDCl₃): 7.10–1.07 (m, 2H), 6.82–6.78 (m, 1H), 3.83 (s, 3H), 3.80 (s, 2H), 2.86 (hep, J=7 Hz, 1H), 1.22 (d, J=7 Hz, 6H).

B. (2R*,4S*,5S*,6S*)-N,N-dimethyl-5-(5-isopropyl-2-methoxybenzyl)amino-6-diphenylmethyl-1-azabicyclo[2.2.2]octane-2-carboxamide (45)

The compound 45 was prepared according to the same procedure as the preparation of compound 35. The compound 45 was isolated as dihydrochloride pentahydrate salt.

M.p.: 168.9°–174.6° C. (dec.).

IR (KBr): 3410, 3190, 2965, 1656, 1505, 1454, 1257, 1029, 710 cm⁻¹.

¹H NMR (CDCl₃) (free form): 7.31–6.98 (m, 11H), 6.64–6.59 (m, 2H), 4.41 (br d, J=12 Hz, 1H), 3.36–3.18 (m, 5H), 3.49 (s, 3H), 3.00–2.95 (m, 1H), 2.80–2.69 (m, 1H), 2.73 (s, 3H), 2.60–2.51 (m, 1H), 2.40–2.35 (m, 1H), 2.22 (br s, 1H), 2.15 (s, 3H), 2.00–1.89 (m, 1H), 1.60–1.50 (m, 1H), 1.30–1.18 (m, 7H).

SYNTHETIC SCHEME FOR EXAMPLES 19-20

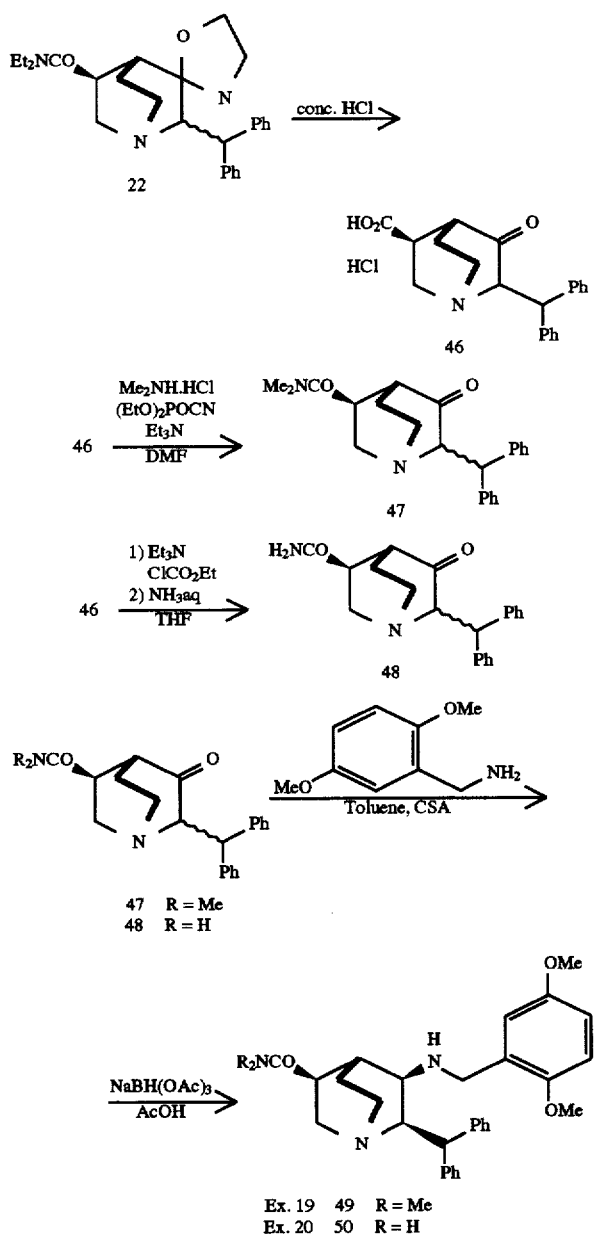

Ex. 19  49  R = Me
Ex. 20  50  R = H

EXAMPLE 19

(3R*,4S*,5S*,6S*)-N,N-Dimethyl-5-(2,5-dimethoxybenzylamino)-6-diphenylmethyl-1-azabicyclo[2.2.2]octane-3-carboxamide (49)

A. (3R*,4S*)-6-Diphenylmethyl-5-oxo-1-azabicyclo[2.2.2]octane-3-carboxylic acid hydrochloride (46)

A solution of (3R*,4S*)-N,N-Diethyl-6-diphenylmethyl-5,5-ethylenedioxy-1-azabicyclo[2.2.2]octane-3-carboxamide (5.2 g, 12 mmol) in 6N-HCl aq (150 ml) was heated at reflux for 18 hours. The resulting precipitate was collected and dried to give 46 (1.7 g, 4.6 mmol, 38%; 46:(3R*,4R*)-isomer=4:1). This was used without further purification.

$^1$H NMR (DMSO-d$_6$): 5.70, 4.81 (d+d, J=11 Hz; a pair of Ph2CHCH and Ph2CHCH).

B. (3R*,4S*) N,N-Dimethyl-6-diphenylmethyl-5-oxo-1-azabicyclo[2.2.2]octane-3-carboxamide (47)

A suspension of 46 (2.1 g, 6.6 mmol) and dimethylamine hydrochloride (0.65 g, 8.0 mmol) in DMF (30 ml) was treated with triethylamine (1.3 g, 13 mmol) at room temperature. To this suspension was added diethyl cyanophosphonate (1.2 g, 7.3 mmol) followed by triethylamine (0.67 g, 6.7 mmol) at room temperature. The mixture was stirred at room temperature for 5 hours, poured into NaHCO$_3$ aq (50 ml) and extracted with EtOAc three times. The combined extracts were dried over Na$_2$SO$_4$ and concentrated. This mixture was purified by a column chromatography on silica gel (hexane:EtOAc=1:4) to give 47 as a single isomer at 3-position (1.4 g, 3.9 mmol, 60%)

$^1$H NMR (CDCl$_3$): 4.49, 4.02 (d+d, J=8 Hz; a pair of Ph2CHCH and Ph2CHCH of one isomer), 4.66, 3.96 (d+d, J=8 Hz; a pair of Ph2CHCH and Ph2CHCH of another isomer).

A mixture of 47 (3.9 g, 10 mmol), 2,5-dimethoxybenzyl amine (1.9 g, 11 mmol) camphor sulfonic acid (120 mg) in toluene (40 ml) was heated at reflux with removal of water for 8 hours and then the solvent was removed. The residue was dissolved in small amount of THF (5 ml) and this solution was added to a solution of sodium triacetoxyborohydride (5.3 g, 25 mmol) in acetic acid (100 ml) at room temperature. The mixture was stirred at room temperature for 4 hours and the solvent was removed. Water (25 ml) was added and the mixture was neutralized with sodium bicarbonate (NaHCO$_3$) and extracted with ethyl acetate (EtOAc) three times. The combined extracts were dried over sodium sulfate (Na$_2$SO$_4$) and concentrated. The crude was purified by recrystallization from EtOAc to give 49 (2.4 g, 4.4 mmol, 44%)

C. (3R*,4S*,5S*,6S*)-N,N-Dimethyl-5-(2,5-dimethoxybenzylamino)-6-diphenylmethyl-1-azabicyclo[2.2.2]octane-3-carboxamide (49)

M.p.: 142.0142.9° C.
IR (KBr): 1637, 1499 cm$^{-1}$.
$^1$H NMR (CDCl$_3$): 7.03–7.37 (m, 10H), 6.68 (dd, J=8.8, 2.5 Hz, 1H), 6.64 (d, J=8.8 Hz, 1H), 6.39 (d, J=2.5 Hz, 1H), 4.51 (d, J=12.1 Hz, 1H), 3.73 (s, 3H), 3.49 (s, 3H), 3.05–3.82 (m, 9H), 2.96 (s, 6H), 2.62–2.95 (m, 4H), 2.17 (br, 1H), 1.62–1.77 (m, 2H).

EXAMPLE 20

(3R*,4S*,5S*,6S*)-5-(2,5-Dimethoxybenzylamino)-6-diphenylmethyl-1-azabicyclo[2.2.2]octane-3-carboxamide (50)

A. (3R*,4S*) N,N-Dimethyl-6-diphenylmethyl-5-oxo-1-azabicyclo[2.2.2]octane-3-carboxamide (48)

A suspension of 46 (1.1 g, 3.3 mmol) in THF (10 ml) was treated with triethylamine (0.66 g, 6.6 mmol) at room temperature. To this suspension was added ethyl chloroformate (0.36 g, 3.3 mmol) at 0° C. After 30 minutes, NH3 aq (0.67 g, 6.7 mmol) was added at 0° C. The mixture was stirred at room temperature for 1 hour, poured into H$_2$O and extracted with EtOAc three times. The combined extracts were dried over Na$_2$SO$_4$ and concentrated to give 48 (1.2 g, 3.0 mmol, 90%; 4:1 mixture of isomers at 3-position). This was used without further purification.

$^1$H NMR (CDCl$_3$): 4.43, 3.98 (d+d, J=9 Hz; a pair of Ph2CHCH and Ph2CHCH of one isomer), 4.51, 4.28 (d+d, J=8 Hz; a pair of Ph2CHCH and Ph2CHCH of another isomer).

B. (3R*,4S*,5S*,6S*)-5-(2,5-Dimethoxybenzylamino)-6-diphenylmethyl-1-azabicyclo[2.2.2]octane-3-carboxamide (50)

A mixture of 48 (1.2 g, 3 mmol), 2,5-dimethoxybenzyl amine (0.6 g, 3.3 mmol) camphor sulfonic acid (45 mg) in toluene (15 ml) was heated at reflux with removal of water for 3 hours and then the solvent was removed. The residue was dissolved in small amount of THF (3 ml) and this solution was added to a solution of sodium triacetoxyborohydride (1.7 g, 8 mmol) in acetic acid (40 ml) at room temperature. The mixture was stirred at room temperature for 3 hours and the solvent was removed. Water was added and the mixture was neutralized with NaHCO$_3$ and extracted with EtOAc three times. The combined extracts were dried over Na$_2$SO$_4$ and concentrated. Recrystallization from MeOH/acetone to give by-product. The mother liquor was concentrated and the residue was purified by recrystallization from MeOH/EtOAc to give 50 (0.27 g, 0.56 mmol, 19%)

M.p.: 127°–129° C.

IR (KBr): 3350, 1686, 1493 cm$^{-1}$.

$^1$H NMR (CDCl$_3$): 7.05–7.32 (m, 10H), 6.69 (dd, J=8.8, 2.5 Hz, 1H), 6.64 (d, J=8.8 Hz, 1H), 6.36 (d, J=2.5 Hz, 1H), 4.47 (d, J=12.1 Hz, 1H), 3.74 (s, 3H), 3.53 (s, 3H), 3.48–3.75 (m, 3H), 2.95–3.26 (m, 6H), 2.11 (br, 1H), 2.59–2.62 (m, 1H), 2.37–2.50 (m, 2H), 1.76–1.89 (m, 1H).

SYNTHETIC SCHEME FOR EXAMPLE 21

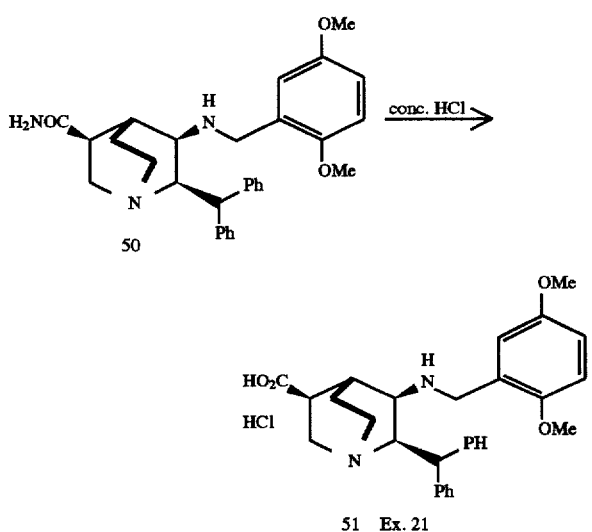

EXAMPLE 21

(3R*,4S*,5S*,6S*)-5-(2,5-Dimethoxybenzylamino)-6-diphenylmethyl-1-azabicyclo[2.2.2]octane-3-carboxylic acid hydrochloride (51)

A solution of compound 50 (100 mg, 0.2 mmol) in conc. HCl (2 ml) was heated at reflux for 15 hours. After cooling down to room temperature, the mixture was basified with NH3 aq and extracted with CH$_2$Cl$_2$ twice. The combined extracts were dried and concentrated. 10% HCl-MeOH was added and evaporated. The resulting precipitate was recrystallized from MeOH-ether to give 51 (30 mg, 0.054 mmol, 27%).

M.p.: 230° C. (dec).

IR (KBr): 2945, 1726, 1502, 1451 cm$^{-1}$.

$^1$H NMR (free base, CDCl$_3$): 6.95–7.32 (m, 10H), 6.65 (dd, J=8.8, 2.5 Hz, 1H), 6.61 (d, J=8.8 Hz, 1H), 6.49 (d, J=2.5 Hz, 1H), 4.41 (d, J=12.1 Hz, 1H), 3.68 (s, 3H), 3.53 (s, 3H), 2.70–3.70 (m, 7H), 2.31–2.60 (m, 3H), 1.67–1.85 (m, 1H), 1.33–1.49 (m, 1H).

EXAMPLE 22

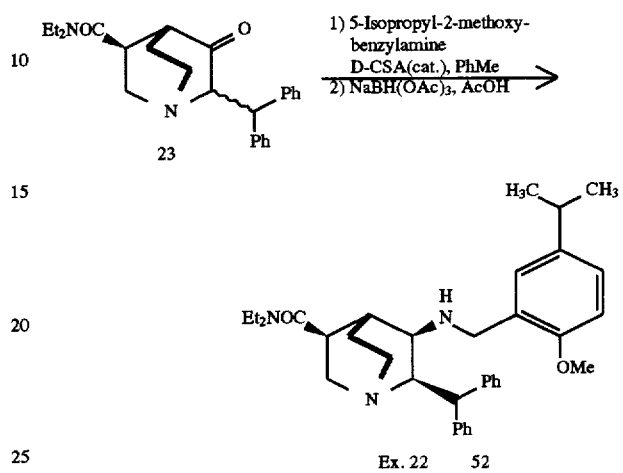

(3R*,4S*,5S*,6S*)-N,N-Diethyl-5-(5-isopropyl-2-methoxybenzylamino)-6-diphenylmethyl-1-azabicyclo[2.2.2]octane-3-carboxamide (52)

The title compound 52 was prepared according to the same procedure as the preparation of compound 24 from compound 23 (Example 9), and isolated as dihydrochloride salt.

IR (free amine, KBr): 3450, 1633, 1499, 1443, 1248, 700 cm$^{-1}$.

$^1$H NMR (free mine, CDCl$_3$): 7.37–7.04 (m, 10H), 7.01 (dd, J=2.8, 6.7 Hz, 1H), 6.65 (d, J=6.7 Hz, 1H), 6.60 (d, J=2.8 Hz, 1H), 4.52 (d, J=12.1 Hz, 1H), 3.70–3.50 (m, 4H), 3.53 (s, 3H), 3.38–3.07 (m, 5H), 2.96 (dd, J=4.2, 7.9 Hz, 1H), 2.90–2.56 (m, 4H), 2.17 (br s, 1H), 1.84–1.73 (m, 2H), 1.20 (d, J=7.3 Hz, 6H), 1.17 (t, J=7.0 Hz, 3H), 1.11 (t, J=7.0 Hz, 3H).

SYNTHETIC SCHEME FOR EXAMPLES 23–24

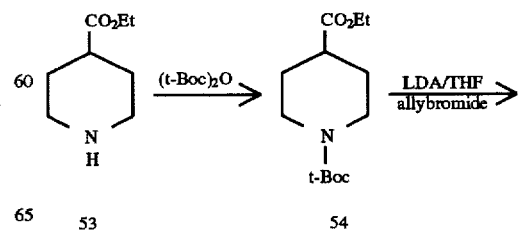

-continued
SYNTHETIC SCHEME FOR EXAMPLES 23-24

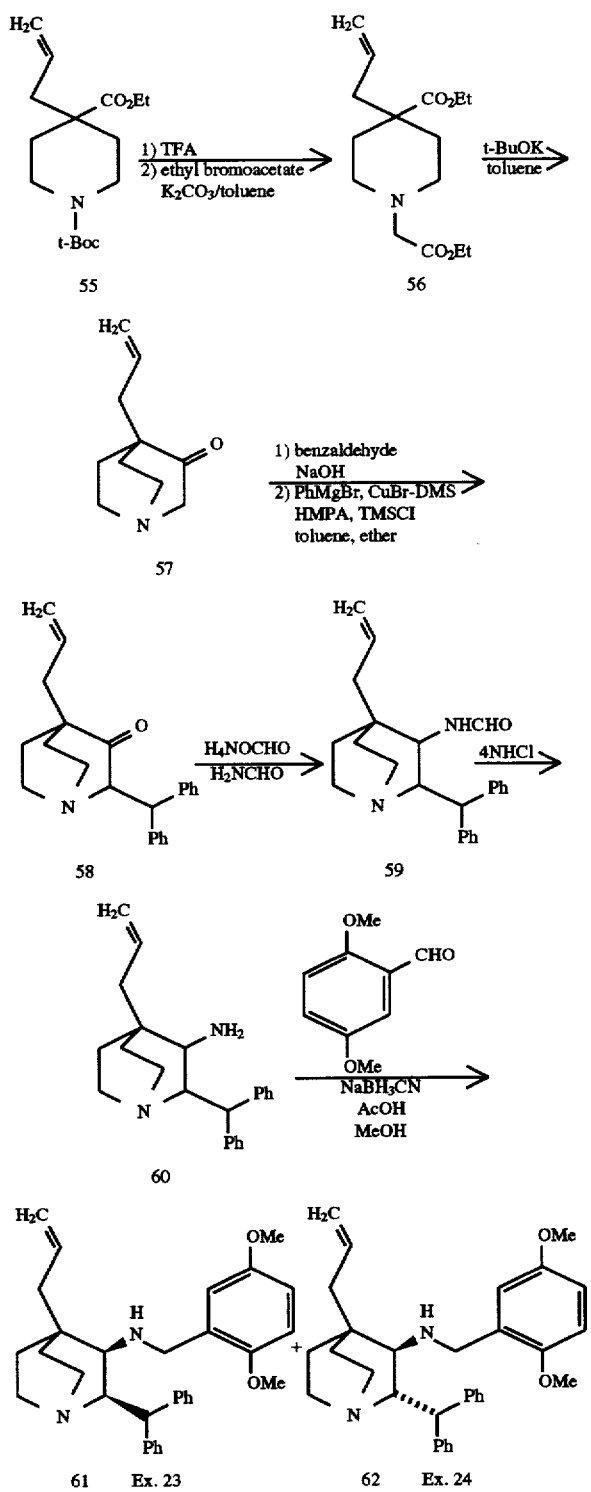

EXAMPLE 23 cis-4-Allyl-3N-(2,5-dimethoxybenzyl)amino-2-diphenylmethyl-1-azabicyclo[2.2.2]octane (61)

A. Ethyl N-Boc-isonipecotate (54)

Ethyl isonipecotate, 53 (25.83 g, 164 mmol) dissolved in 20 ml of THF was slowly added to a solution of di-t-butyl dicarbonate (37.2 g, 70 mmol) at room temperature. The reaction immediately proceeded, and evolution of CO2 was observed. The solvent was removed by evaporation, and the residue was distilled under vacuum. After a forerun (80°–100° C.) was removed, a fraction at 120° C. at 1.5 mm Hg was collected to provide 38.3 g of ethyl N-Boc-isonipecotate, 64 (151 mmol, 92%).

$^1$H NMR (CDCl$_3$): 4.14 (q, J=7 Hz, 2H), 4.02 (br d, 2H), 2.83 (br t, 2H), 2.43 (tt, J=10.9, 3.9 Hz, 1H), 1.87 (m, 2H), 1.64 (m, 2H), 1.46 (s, 9H), 1.26 (t, J=7 Hz, 3H).

B. 4-Allyl-1-azabicyclo[2.2.2]octan-3-one (57)

Ethyl N-Boc-isonipecotate, 54 (33.56 g, 131 mmol) dissolved in 15 ml of THF was slowly added to LDA prepared from diisopropylamine (25.2 ml, 179 mmol), n-butyl lithium (1.59M in hexane, 96 ml, 153 mmol) and 300 ml of THF at −60° C. The rate of addition was controlled by keeping the inner temperature below −60° C. After addition was completed the reaction mixture was warmed up to −25° C., and then cooled back to −60° C. Allyl bromide (12.4 ml, 143 mmol) was added to the enolate solution (<−60° C.), and the mixture was warmed up to −5° C. After the reaction was quenched with acetic acid (17.6 ml) at −60° C., the solvent was removed by evaporation. The residue was worked-up by an ordinal procedure (extraction with ethyl acetate at pH=6.0, washing with brine, drying over Na$_2$SO$_4$, concentration by evaporation) to provide a crude product (40.13 g) of ethyl N-Boc-4-allyl-isonipecotate 55.

$^1$H NMR (CDCl$_3$): 5.68 (m, 1H), 5.08–6.00 (m, 2H), 4.17 (q, J=7.1 Hz, 2H), 3.86 (br d, J=13 Hz, 2H), 2.90 (m, 2H), 2.27 (d, J=7.3 Hz, 2H), 2.07 (m, 2H), 1.45 (s, 9H), 1.38 (m, 2H), 1.26 (t, J=7.1 Hz, 3H).

The obtained crude product was diluted with 20 ml of ethyl acetate, and mixed with 60 ml of trifluoroacetic acid. After 4 hours at room temperature, the resulting mixture was concentrated down by evaporation, and subsequently by co-evaporation with toluene to afford ethyl 4-allyl-isonipecotate as a trifluoroacetic acid (TFA) salt.

$^1$H NMR (CDCl$_3$): 8.60 (br s, 1H), 8.30 (br s, 1H), 5.68–5.56 (m, 1H), 5.15–5.06 (m, 2H), 4.22 (q, J=7.1 Hz, 2H), 3.39 (br.d, J=12 Hz, 2H), 2.99 (m, 2H), 2.35–2.31 (m, 4H), 1.73 (m, 2H), 1.29 (t, J=7.1 Hz, 3H).

The crude TFA salt of ethyl 4-allyl-isonipecotate and ethyl bromoacetate (23.5 g, 141 mmol) were dissolved in toluene. To this solution was added anhydrous K$_2$CO$_3$ (70.7 g, 512 mmol), and the resulting suspension was warmed to 80° C. for 15 minutes. The reaction mixture was cooled down, and adjusted at pH=8.0 with dil.HCl. The resulting solution was worked-up by an ordinal procedure (extraction with ethyl acetate, washing with brine, drying over Na$_2$SO$_4$, concentration by evaporation) to provide 37.4 g of crude ethyl 4-allyl-N-ethoxycarbonylmethyl-isonipecotate, 56.

$^1$H NMR (CDCl$_3$): 5.68 (m, 1H), 5.06–4.99 (m, 2H), 4.22–4.12 (m, 4H), 3.19 (s, 2H), 2.83 (m, 2H), 2.35–2.21 (m, 4H), 2.15 (d, J=13 Hz, 2H), 1.61 (m, 2H), 1.264 (t, J=7 Hz, 3H), 1.256 (t, J=7 Hz, 3H).

Potassium t-butoxide (35.64 g, 320 mmol) was suspended in 100 ml of toluene and heated at reflux. To this suspension was gradually added the crude ethyl 4-allyl-N-ethoxy carbonylmethylisonipecotate 56 obtained above. The reaction was quenched with 120 ml of water, and heated at 80° C. overnight. 6N-HCl (54 ml) was added to the mixture, which was stirred for 15 minutes. The reaction mixture was cooled down to room temperature, and was adjusted at pH=8.0 with dilute (dil.) HCl. The resulting solution was worked-up by an ordinal procedure (extraction with methylene chloride at pH=13.5, washing with brine, drying over Na$_2$SO$_4$, concentration by evaporation) to provide a crude quinuclidine product, which was distilled under vacuum. A fraction at 122° C. at 15 mm Hg was collected to afford 4-allyl-1-azabicyclo[2.2.2]octane-3-one 57 (15.35 g, 72% from 54).

$^1$H NMR (CDCl$_3$): 5.78 (m, 1H), 5.08–4.98 (m, 2H), 3.26 (s, 2H), 3.01 (m, 4H), 2.20 (d, J=7.4 Hz, 2H), 1.95–1.65 (m, 4H).

$^{13}$C NMR (CDCl$_3$): 218.4, 133.6, 117.1, 62.0, 47.0, 42.3, 37.2, 29.4.

C. 4-Allyl-2-diphenylmethyl-1-azabicyclo[2.2.2]octane-3-one (58)

4-Allyl-1-azabicyclo[2.2.2]octan-3-one, 57 (17.66 g, 107 mmol), benzaldehyde (12.49 g, 117 mmol) and sodium hydroxide (0.46 g, 11.5 mmol) were dissolved in 80 ml of ethanol, and the resultant mixture was heated at reflux for 1 hour. After the mixture was cooled down, yellow solids were collected to provide 4-allyl-2-benzylidene-1-azabicyclo[2.2.2]octane-3-one (26.66 g, 98%).

$^1$H NMR (CDCl$_3$): 8.04–8.01 (m, 2H), 7.40–7.32 (m, 3H), 7.03 (s, 1H), 5.87 (m, 1H), 5.09–5.02 (m, 2H), 3.24–2.96 (m, 4H), 2.32 (d, J=7.4 Hz, 2H), 1.97–1.74 (m, 4H).

Copper(I) bromide dimethyl sulfide complex (1.06 g, 5.16 mmol) and 100 ml of toluene were placed in a reaction vessel, which was immersed into an dry-ice acetone bath. Phenylmagnesium bromide (3.0M in ether, 42 ml, 126 mmol) was slowly added to the copper catalyst keeping the inner temperature below –60° C. To this yellow-white suspension was added a solution prepared from 4-allyl-2-benzylidene-1-azabicyclo[2.2.2]octane-3-one (25.9 g, 103 mmol), trimethylsilyl chloride (31.4 ml, 247 mmol), HMPA (43 ml, 247 mmol) and toluene (120 ml) keeping below –60° C. After addition was completed, the reaction mixture was warmed up to 0° C. The reaction was quenched with 14.5 ml of acetic acid at –60° C. Water was added to the reaction mixture, which was neutralized with Na$_2$CO$_3$ (pH=6.5). The resulting solution was worked-up by an ordinal procedure (extraction with ether at pH=6.5, and then at pH=8.0, washing with brine, drying over Na$_2$SO$_4$, concentration by evaporation) to provide a crude product, which was triturated with ether to afford 4-allyl-2-diphenylmethyl-1-azabicyclo[2.2.2]octane-3-one, 58 (23.04 g, 68%).

$^1$H NMR (CDCl$_3$): 7.39–7.15 (m, 10H), 5.72 (m, 1H), 5.04–4.95 (m, 2H), 4.47 (d, J=8.4 Hz, 1H), 3.96 (d, J=8.4 Hz, 1H), 3.11 (m, 2H), 2.65 (m, 2H), 2.16 (m, 2H), 1.94–1.6 (m, 4H).

$^{13}$C NMR (CDCl$_3$): 219.3, 143.1, 142.2, 134.3, 128.3, 126.5, 126.4, 117.5, 72.3, 50.6, 50.0, 44.0, 42.4, 37.9, 31.1, 29.9.

4-Allyl-2-diphenylmethyl-1-azabicyclo[2.2.2]octan-3-one 58 (4.00 g, 12.1 mmol) and ammonium formate (8.00 g, 127 mmol) were dissolved in 24 ml of formamide, and the resulting solution was heated at 170° C. (bath temperature) for 5 hours. The solvent was removed under vacuum, and water was added to the residue. The obtained solids were purified by recrystallization from methanol to provide a mixture (c.a. 1:1) of cis and trans 4-allyl-2-diphenylmethyl-3-formamido-1-azabicyclo[2.2.2]octane, 59 (2.03 g, 70%).

$^1$H NMR (CDCl$_3$): 6.69 (d, J=11.4 Hz), 6.52 (d, J=11.7 Hz).

MS: 360 (M+), 319.

The above formamide, 59 was dissolved in 20 ml of 4N-HCl, and the resultant solution was heated at 80° C. overnight. The reaction was quenched with Na$_2$CO$_3$ aq. The resulting solution was worked-up by an ordinal procedure (extraction with methylene chloride, drying over Na$_2$SO$_4$, concentration by evaporation) to provide a mixture of cis and trans isomer of 4-allyl-2-diphenylmethyl-1-azabicyclo[2.2.2]octane-3-amine, 60 (1.95 g).

MS: 332 (M+), 291, 166.

E. cis-4-Allyl-3N-(2,5-dimethoxybenzyl)amino-2-diphenylmethyl-1-azabicyclo[2.2.2]octane (61)

The above crude amine 60 and 2,5-dimethoxybenzaldehyde (1.19 g, 6.99 mmol) were dissolved in methanol. A trace amount of Bromocresol Green and sodium cyanoborohydride (380 mg, 6.05 mmol) were added to the mixture, and pH of the reaction mixture was adjusted as acidic with acetic acid. After overnight, the reaction mixture was basified with Na$_2$CO$_3$ aq, and worked-up by an ordinal procedure (extraction with CH$_2$Cl$_2$, washing with brine, drying over Na$_2$SO$_4$, concentration by evaporation) to provide a crude mixture, which was purified by column chromatography (silica-gel, 0 to 10% MeOH/CH$_2$Cl$_2$) to provide partially separated fractions of cis (61) and trans (62) isomers. Recrystallization of fractions enriched by a more polar isomer from methanol to afford pure cis isomer 61 (280 mg). The less polar isomer 62 was converted to the dimesylate salt and then purification by recrystallization from acetone to give pure trans isomer (395 mg).

M.p.: 163.7°–164.8° C.

IR (nujol): 1594, 1498, 1029 cm$^{-1}$.

$^1$H NMR (CDCl$_3$): 7.40–7.02 (m, 10H), 6.70 (m, 2H), 6.40 (br s, 1H), 5.77 (m, 1H), 5.04–4.97 (m, 2H), 4.59 (d, J=11.9 Hz, 1H), 3.77–3.68 (m, 7H, including 3.77 (s, 3H), 3.72 (s, 3H) and 3.34 (d, J=11.4 Hz, 1H)), 2.98 (m, 1H), 2.88–2.56 (m, 4H), 2.25–2.04 (m, 3H), 1.57–1.40 (m, 3H), 1.25 (m, 1H).

EXAMPLE 24 trans-4-Allyl-3N-(2,5-dimethoxybenzyl)amino-2-diphenylmethyl-1-azabicyclo[2.2.2]octane (62)

The title compound 62 was prepared as indicated in Example 23 E above.

M.p.: 245.0°–246.1° C.

IR (nujol): 1609, 1502, 1044 cm$^{-1}$.

$^1$H NMR (CDCl$_3$): 7.44–7.09 (m, 10H), 6.71–6.63 (m, 2H), 6.52 (d, J=1.5 Hz, 1H) 5.76 (m, 1H), 5.05–4.94 (m, 2H), 3.90 (d, J=11.9 Hz, 1H), 3.75(s, 3H), 3.71 (s, 3H), 3.31 (dd, J=11.9, 3.5 Hz; 1H), 3.00 (d, J=12.4 Hz, 1H), 2.96–2.83 (m, 3H), 2.52–2.40 (m, 1H), 2.40 (d, J=12.4 Hz, 1H), 2.24 (br.s, 1H), 2.18–2.02 (m, 2H), 1.66–1.13 (m, 4H).

The title compounds of Examples 25–33 were prepared according to the procedure described in Example 9.

EXAMPLE 25

(3R*,4S*,5S*,6S*)-N,N-Diethyl-5-(5-ethyl-2-methoxybenzylamino)-6-diphenylmethyl-1-azabicyclo[2.2.2]octane-3-carboxamide dihydrochloride M.p.: 190°–193° C.

IR (KBr, free amine): 1609, 1502, 1044 cm$^{-1}$.

$^1$H NMR (CDCl$_3$, free amine): 7.39–7.04 (m, 11H), 6.98 (dd, J=8.4, 2.0 Hz, 1H), 6.63 (d, J=8.4 Hz, 1H), 6.50 (d, J=2.0 Hz, 1H), 3.83–3.46 (m, 3H), 3.51 (s, 3H), 3.35–3.08 (m, 6H), 2.96 (q, J=4.0 Hz, 1H), 3.31 (dd, J=11.9, 3.5 Hz, 1H), 3.00 (d, J=12.4 Hz, 1H), 2.96–2.83 (m, 3H), 2.52–2.40 (m, 1H), 2.40 (d, J=12.4 Hz, 1H), 2.24 (br.s, 1H), 2.18–2.02 (m, 2H), 1.66–1.13 (m, 4H).

EXAMPLE 26

(3R*,4S*,5S*,6S*)-N,N-Diethyl-5-(2-methoxy-5-methylthiobenzylamino)-6-diphenylmethyl-1-azabicyclo[2.2.2]octane-3-carboxamide dihydrochloride M.p.: 158°–163° C.

IR (KBr, free amine): 3450, 1630, 1597, 1487, 1443, 1244, 1029, 813, 750, 701, 696 cm$^{-1}$.

$^1$H NMR (CDCl$_3$, free amine): 7.35–7.04 (m, 11H), 6.76 (d, J=2.2 Hz, 1H), 6.65 (d, J=8.8 Hz, 1H), 4.50 (d, J=12.1 Hz, 1H), 3.68–3.52 (m, 4H), 3.50 (s, 3H), 3.33–3.06 (m, 5H), 2.90 (q, 1H), 2.83–2.56 (m, 3H), 2.42 (s, 3H), 2.11 (br s, 1H), 1.80–1.65 (m, 2H), 1.17 (t, J=7.0 Hz, 3H), 1.11 (t, J=7.0 Hz, 3H).

EXAMPLE 27

(3R*,4S*,5S*,6S*)-N,N-Diethyl-5-(2-methoxy-5-trifluoromethoxybenzylamino)-6-diphenylmethyl-1-azabicyclo[2.2.2]octane-3-carboxamide M.p.: 122°–125° C.

IR (KBr, free amine): 3450, 1634, 1499, 1465, 1252, 1153, 1031, 752, 704, 604 cm$^{-1}$.

$^1$H NMR (CDCl$_3$, free amine): 7.36–6.99 (m, 10H), 6.66 (d, J=9.2 Hz, 1H), 6.55 (d, J=2.6 Hz, 1H), 4.48 (d, J=12.1 Hz, 1H), 3.70–3.47 (m, 4H), 3.56 (s, 3H), 3.33–3.05 (m, 5H), 2.91 (dd, J=4.0, 7.9 Hz, 1H), 2.85–2.58 (m, 3H), 2.11 (br s, 1H), 1.90–1.55 (m, 2H), 1.15 (t, J=7.1 Hz, 3H), 1.10 (t, J=7.1 Hz, 3H).

EXAMPLE 28

(3R*,4S*,5S*,6S*)-N,N-Diethyl-5-(5-chloro-2-methoxybenzylamino)-6-diphenylmethyl-1-azabicyclo[2.2.2]octane-3-carboxamide dihydrochloride M.p.: 190°–194° C.

IR (KBr, free amine): 3430, 1631, 1486, 1449, 1247, 1025, 821, 751, 701, 693 cm$^{-1}$.

$^1$H NMR (CDCl$_3$, free amine): 7.58 (d, J=6.9 Hz, 2H), 7.40–7.19 (m, 7H), 7.14 (dd, J=2.5, 8.9 Hz, 1H), 6.63 (d, J=8.9 Hz, 2H), 5.24 (br s, 1H), 4.49 (d, J=11.9 Hz, 1H), 3.85–3.06 (m, 12H), 3.47 (s, 3H), 2.24 (br s, 1H), 2.15–1.90 (m, 2H), 1.23 (t, J=7.2 Hz, 3H), 1.02 (t, J=7.2 Hz, 3H).

EXAMPLE 29

(3R*,4S*,5S*,6S*)-N,N-Diethyl-5-(5-t-butyl-2-methoxybenzylamino)-6-diphenylmethyl-1-azabicyclo[2.2.2]octane-3-carboxamide dihydrochloride M.p.: 180°–183° C.

IR (KBr, free amine): 3450, 1630, 1500, 1457, 1450, 1250, 751, 702 cm$^{-1}$.

$^1$H NMR (CDCl$_3$, free amine): 7.36–7.03 (m, 10H), 6.89 (d, J=2.6 Hz, 1H), 6.64 (d, J=8.5 Hz, 1H), 4.52 (d, J=12.1 Hz, 1H), 3.71–3.48 (m, 4H), 3.52 (s, 3H), 3.35–3.03 (m, 5H), 2.98 (dd, J=4.0, 7.7 Hz, 1H), 2.91–2.60 (m, 3H), 2.19 (br s, 1H), 1.87–1.75 (m, 2H), 1.27 (s, 9H), 1.16 (t, J=7.3 Hz, 3H), 1.11 (t, J=7.3 Hz, 3H).

EXAMPLE 30

(3R*,4S*,5S*,6S*)-5-(2-methoxy-5-methylthiobenzylamino)-6-diphenylmethyl-1-azabicyclo[2.2.2]octane-3-carboxylic acid dihydrochloride M.p.: 170°–175° C.

IR (KBr, free amine): 3420, 1725, 1490 cm$^{-1}$.

$^1$H NMR (CDCl$_3$, free amine): 7.40 (m, 11H), 6.75 (br s, 1H), 6.41 (d, J=8.4 Hz, 1H), 4.40 (d, J=11.7 Hz, 1H), 4.05 (br s, 1H), 3.48 (s, 3H), 3.60–3.40 (m, 2H), 3.34–2.50 (m, 8H), 2.38 (s, 3H), 1.95 (s, 3H), 1.95–1.56 (m, 2H).

EXAMPLE 31

(3R*,4S*,5S*,6S*)-5-(5-Isopropyl-2-methoxybenzylamino)-6-diphenylmethyl-1-azabicyclo[2.2.2]octane-3-carboxamide dihydrochloride M.p.: 247° C.

IR (KBr, free amine): 3310, 1685, 1505 cm$^{-1}$.

$^1$H NMR (CDCl$_3$, free amine): 7.35–7.00 (m, 11H), 6.66 (d, J=8.4 Hz, 1H), 6.57 (d, J=2.2 Hz, 1H), 5.39 (br s, 2H), 4.48 (d, J=12.1 Hz, 1H), 3.70–3.64 (m, 1H), 3.63 (d, J=12.8 Hz, 1H), 3.55 (s, 3H), 3.20 (d, J=12.8 Hz, 1H), 3.19–2.93 (m, 4H), 2.83–2.60 (m, 2H), 2.49–2.42 (m, 2H), 1.95–1.81 (m, 1H), 1.60–1.50 (m, 1H), 1.20 (d, J=6.6 Hz, 3H), 1.18 (d, J=6.6 Hz, 3H).

EXAMPLE 32

(3R*,4S*,5S*,6S*)-5-(5-Isopropyl-2-methoxybenzylamino)-6-diphenylmethyl-1-azabicyclo[2.2.2]octane-3-carboxylic acid dihydrochloride M.p.: 150°–155° C.

IR (KBr, free amine): 3400, 1730, 1510 cm$^{-1}$.

$^1$H NMR (CDCl$_3$, free amine): 7.35–7.00 (m, 11H), 6.63 (d, J=8.8 Hz, 1H), 6.57 (d, J=8.4 Hz, 1H), 4.47 (d, J=12.4 Hz, 1H), 4.00 (br s, 1H), 3.51 (s, 3H), 3.70–3.45 (m, 2H), 3.40–2.40 (m, 8H), 2.00–1.55 (m, 2H), 1.19 (d, J=6.9 Hz, 3H), 1.18 (d, J=6.9 Hz, 3H).

EXAMPLE 33

(3R*,4S*,5S*,6S*)-5-(2-Methoxy-5-methylthiobenzylamino)-6-diphenylmethyl-1-azabicyclo[2.2.2]octane-3-carboxamide dihydrochloride M.p.: 220°–225° C.

IR (KBr): 3300, 3200, 1685, 1495 cm$^{-1}$.

$^1$H NMR (CDCl$_3$, free amine): 7.34–7.06 (m, 11H), 6.72 (d, J=2.6 Hz, 1H), 6.67 (d, J=8.4 Hz, 1H), 5.48 (br.s, 2H), 4.45 (d, J=12.1 Hz, 1H), 3.80–3.64 (m, 1H), 3.62–3.50 (m, 4H), 3.28–2.95 (m, 4H), 3.28–2.95 (m, 6H), 2.63–2.76 (m, 1H), 2.57–2.45 (m, 1H), 2.42 (s, 3H), 1.95–1.50 (m, 2H).

SYNTHETIC SCHEME FOR EXAMPLE 34

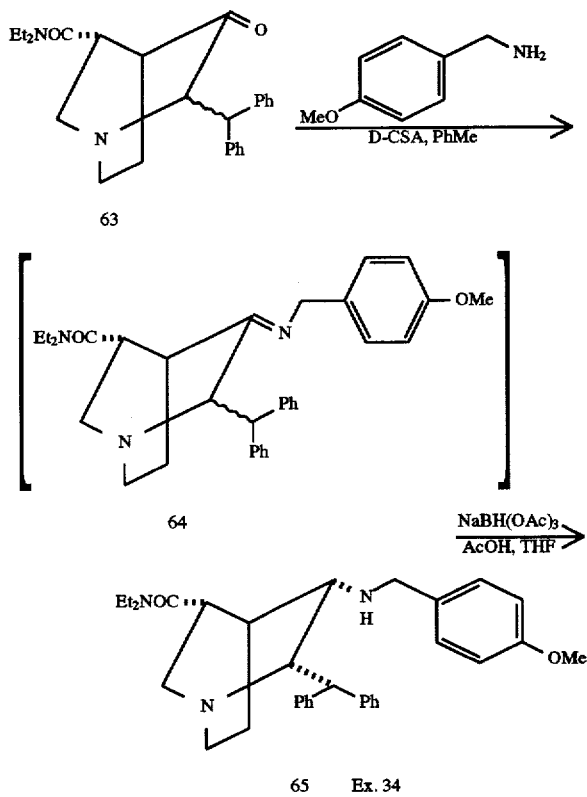

EXAMPLE 34

(2R*,3R*,4R*,5S*)-N,N-Diethyl-5-[N-(4-methoxybenzyl)amino]-6-diphenylmethyl-1-azabicyclo[2.2.2]octane-3-carboxamide (65)

To a suspension of ketone, 63 (0.30 g, 0.77 mmol) and 4-methoxybenzylamine (0.12 ml, 0.89 mmol) in dry toluene (5.0 ml) was added D-camphorsulfonic acid (9.2 mg, 0.04 mmol). The resulting mixture was stirred and heated at reflux through a side-armed dropping funnel packed with molecular sieves 4 to remove water azeotropically. After stirring under the above heating conditions overnight, the reaction mixture was concentrated in vacuo to dryness to give crude imine, 64. This was dissolved in dry THF (1.0 ml), and the solution was added dropwise to a stirred solution of sodium triacetoxyborohydride (0.41 g, 1.93 mmol) in acetic acid (8.0 ml) at room temperature. After stirring at room temperature for 8 hrs, the reaction mixture was concentrated in vacuo. The residue was basified with NaOH aq., and extracted with chloroform ($CHCl_3$). The combined $CHCl_3$ extracts were washed with sat. NaCl aq., dried ($K_2CO_3$), and concentrated in vacuo to give a pale yellow viscous oil (0.52 g). This was chromatographed over silica gel (Merck Kieselgel 60, 8.0 g). Elution with methylene chloride-methanol ($CH_2Cl_2$-MeOH) (100:1) gave 65, contaminated with a trace amount of its endo isomer, as a colorless viscous oil, which crystallized spontaneously on standing. The solid was recrystallized from 2-propanol to give pure 65 (65.5 mg, 17%) as colorless prisms.

M.p.: 131°–133° C. (isopropanol).

IR (nujol): 3380(m), 1645(s), 1610(m), 1510(s), 1243(s), 1030(s), 810(m), 750(m), 745(m), 710(m), 690(m) $cm^{-1}$.

$^1H$ NMR ($CDCl_3$): 7.43–7.15 (m, 9H), 7.15–7.04 (m, 1H), 6.68 (d, J=8.8 Hz, 2H), 6.50 (d, J=8.8 Hz, 2H), 4.43 (d, J=12.1 Hz, 1H), 3.78 (s, 3H), 3.77–3.62 (m, 1H), 3.56 (d, J=13.0 Hz, 1H), 3.56–3.44 (m, 1H), 3.16 (d, J=13.0 Hz, 1H), 3.35–3.04 (m, 6H), 2.84 (dd, J=4.0, 7.7 Hz, 1H), 2.80–2.65 (m, 1H), 2.59 (dd, J=8.6, 8.6 Hz, 1H), 2.08 (br s, 1H), 1.86–1.68 (m, 2H), 1.63 (br s, NH, 1H), 1.15 (t, J=7.1 Hz, 3H), 1.11 (t, J=7.1 Hz, 3H).

SYNTHETIC SCHEME FOR EXAMPLES 35–37

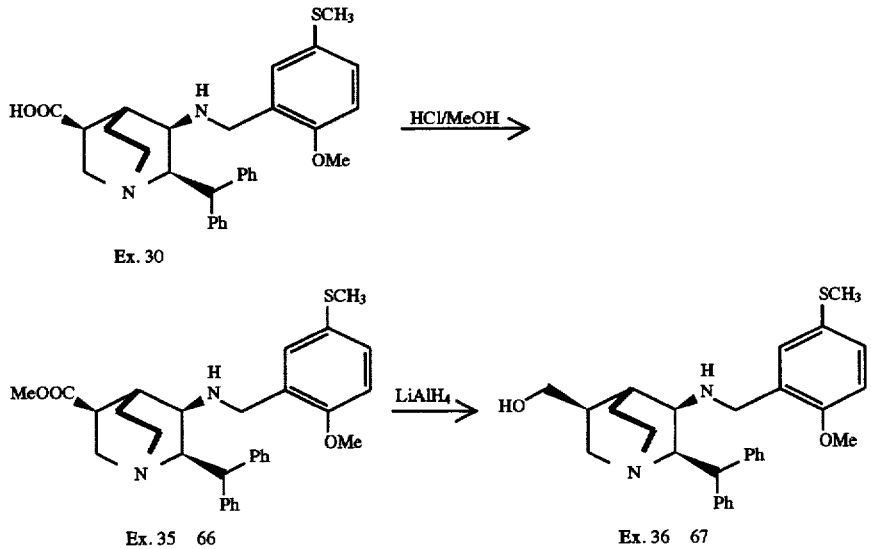

-continued
SYNTHETIC SCHEME FOR EXAMPLES 35–37

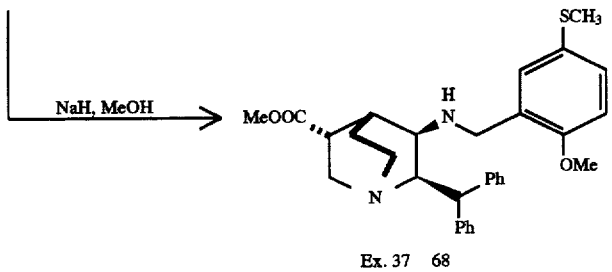

Ex. 37  68

EXAMPLE 35

(3R*,4S*,5S*,6S*)-Methyl-6-diphenylmethyl-5-(2-methoxy-5-methylthiobenzyl(amino)-1-azabicyclo[2.2.2]octane-3-carboxylate (66)

A solution of (3R*,4S*,5S*,6S*)-N,N-Diethyl-5-(2-methoxy-5-methylthiobenzylamino)-6-diphenylmethyl-1-azabicyclo[2.2.2]octane-3-carboxylic acid (the title compound of Example 30, 0.40 g, 0.65 mmol) in 10% HCl/MeOH (5 ml) was heated at reflux for 2 hours. After cooling down to room temperature the solvent was removed. The NaHCO$_3$ aq solution was added (pH=8), the organic layer was extracted with EtOAc (70 ml) twice. The combined extracts were washed with brine, dried (MgSO$_4$) and evaporated. The residue was chromatographed on silica gel by using hexane:EtOAc=3:2 as eluent to give 66 (0.20 g, 56%).

M.p.: 70°–73° C.

IR (KBr): 3440, 2950, 1730, 1495 cm$^{-1}$.

$^1$H NMR (CDCl$_3$, free amine): 7.30–7.05 (m, 11H), 6.72 (d, J=2.2 Hz, 1H), 6.65 (d, J=8.4 Hz, 1H), 4.43 (d, J=12.1 Hz, 1H), 3.71 (s, 3H), 3.55 (s, 3H), 3.65–3.52 (m, 3H), 3.24 (d, J=13.2 Hz, 1H), 3.20–2.92 (m, 4H), 2.66–2.43 (m, 3H), 2.42 (s, 3H), 1.92–1.75 (m, 1H), 1.50–1.32 (m, 1H).

EXAMPLE 36

(3R*,4S*,5S*,6S*)-6-diphenylmethyl-3-hydroxymethyl-5-(2-methoxy-5-methylthiobenzylamino)-1-azabicyclo[2.2.2]octane dihydrochloride (67)

To a suspension of LiAlH$_4$ (12 mg, 0.39 mmol) in ether (5 ml) was added 66 (66 mg, 0.13 mmol) at 0° C., then stirred at room temperature for 1 hour. The NaHCO$_3$ aq. solution (2 drops) and then EtOAc (20 ml) were added and stirred for 15 minutes. The organic layer was separated, dried (MgSO$_4$) and evaporated under reduced pressure. The crude product was treated with 10% HCl/MeOH to give 67 (43 mg, 55%)

M.p.: 178°–182° C.

IR (KBr): 3400, 1575, 1495 cm$^{-1}$.

$^1$H NMR (CDCl$_3$, free amine): 7.34–7.07 (m, 11H), 6.73 (d, J=2.2 Hz, 1H), 6.64 (d, J=8.4 Hz, 1H), 4.45 (d, J=12.1 Hz, 1H), 3.54 (s, 3H), 3.76–3.52 (m, 5H), 3.20 (d, J=12.8 Hz, 1H), 3.21–3.20 (m, 1H), 2.98–2.86 (m, 2H), 2.60–2.47 (m, 1H), 2.42 (s, 3H), 2.30–2.19 (m, 2H), 2.00–1.72 (m, 2H), 1.39–1.30 (m, 1H).

EXAMPLE 37

(3R*,4R*,5R*,6R*)-Methyl-5-(2-methoxy-5-methylthiobenzylamino)-6-diphenylmethyl-1-azabicyclo[2.2.2]octane-3-carboxylic acid dihydrochloride (68)

To a solution of 66 (0.141 g, 0.25 mmol) in dry MeOH (3 ml) was added 60%-NaH (20 mg, 0.50 mmol) in one portion at room temperature. The mixture was heated at 50° C. for 2 hours. The solvent was removed, extracted with EtOAc (100 ml). The organic layer was washed with brine, dried (MgSO$_4$) and evaporated. The residue was chromatographed on silica gel by using hexane: EtOAc=1:1 as eluent to give 68 (28 mg, 20%).

M.p.: 144°–147° C.

IR (KBr): 3420, 1730, 1495 cm$^{-1}$.

$^1$H NMR (CDCl$_3$, free amine): 7.29–7.05 (m, 11H), 6.74 (d, J=2.2 Hz, 1H), 6.61 (d, J=8.4 Hz, 1H), 4.41 (d, J=12.1 Hz, 1H), 3.84 (dd, J=7.3, 12.1 Hz, 1H), 3.72–3.62 (m, 1H), 3.68 (s, 3H), 3.48 (s, 3H), 3.58–3.49 (m, 2H), 3.31 (dt, J=2.7, 13.6 Hz, 1H), 3.15 (d, J=13.6 Hz, 1H), 2.87–2.75 (m, 2H), 2.70–2.62 (m, 1H), 2.62–2.48 (m, 2H), 2.41 (s, 3H), 2.11–1.97 (m, 1H).

EXAMPLE 38

(2R*,4R*,5R*,6R*)-N,N-Dimethyl-6-diphenylmethyl-5-(2-methoxy-5-methylthiobenzylamino)-1-azabicyclo-[2.2.2]octane-2-carboxamide The title compound of Example 38 was treated in the same manner used for the preparation of compound 39 (Ex. 15).

M.p.: 156°–158° C.

IR (KBr): 3450, 2920, 1645, 1495 cm$^{-1}$.

$^1$H NMR (CDCl$_3$, free amine): 7.36–6.98 (m, 11H), 6.74 (d, J=2.6 Hz, 1H), 6.63 (d, J=8.4 Hz, 1H), 4.51 (d, J=12.1 Hz, 1H), 3.55 (d, J=13.2 Hz, 1H), 3.52–3.49 (m, 1H), 3.49 (s, 3H), 3.35 (d, J=8.4 Hz, 1H), 3.21 (d, J=13.2 Hz, 1H), 3.19–3.00 (m, 1H), 2.97–2.92 (m, 1H), 2.79 (s, 3H), 2.66–2.59 (m, 1H), 2.41 (s, 3H), 2.20–2.10 (m, 1H), 2.17 (s, 3H), 1.82–1.67 (m, 1H), 1.48–1.30 (m, 2H).

EXAMPLE 39

(2R*,4R*,5R*,6R*)-6-Diphenylmethyl-5-(2-methoxy-5-methylthiobenzylamino)-1-azabicyclo[2.2.2]octane-2-carboxylic acid dihydrochloride The title compound of Example 39 was treated in the same manner used for the preparation of compound 24 (Ex. 9).

M.p.: 162°–167° C.

IR (KBr): 3430, 1740, 1495 cm$^{-1}$.

$^1$H NMR (CDCl$_3$): 7.36–7.25 (m, 10H), 7.14 (dd, J=2.6, 8.4 Hz, 1H), 6.71 (d, J=2.6 Hz, 1H), 6.67 (d, J=8.4 Hz, 1H), 4.65 (d, J=12.1 Hz, 1H), 4.26 (dd, J=8.4, 12.1 Hz, 1H), 3.79–3.67 (m, 1H), 3.53 (s, 3H), 3.50–3.20 (s, 3H), 3.10–2.80 (m, 1H), 2.70–2.57 (m, 1H), 2.42 (s, 3H), 2.33–2.15 (m, 1H), 1.72–1.60 (m, 1H).

The title compounds of Examples 40, 41 and 42 were treated in the same manner used for the preparation of compounds 49 and 50 (Ex. 19 and 20).

EXAMPLE 40

(3R*,4S*,5S*,6S*)-N-Methoxy-N-methyl-5-(2,5-dimethoxybenzylamino)-6-diphenylmethyl-1-azabicyclo[2.2.2]octane-3-carboxamide dihydrochloride M.p.: 174°–176° C.

IR (KBr): 3415, 2945, 1658, 1504, 1454, 1436, 1391, 1232, 1041, 711 cm$^{-1}$.

$^1$H NMR (CDCl$_3$, free base): 7.35–7.05 (m, 10H), 6.67 (dd, J=2.9, 8.2 Hz, 1H), 6.60 (d, J=8.8 Hz, 1H), 6.42 (d, J=2.9 Hz, 1H), 4.52 (d, J=12.1 Hz, 1H), 3.73 (s, 3H), 3.67 (s, 3H), 3.47 (s, 3H), 3.20 (s, 3H), 3.83–2.80 (m, 8H), 2.71–2.60 (m, 1H), 2.36 (br, 1H), 1.85–1.25 (m, 2H).

EXAMPLE 41

(3R*,4S*,5R*,6R*)-N-Ethyl-5-(2,5-dimethoxybenzylamino)-6-diphenylmethyl-1-azabicyclo[2.2.2]octane-3-carboxamide dihydrochloride M.p.: 248°–249° C.

IR (KBr): 3480, 3480, 3250, 3195, 2975, 1675, 1594, 1506, 1453, 1436, 1238, 712 cm$^{-1}$.

$^1$H NMR (CDCl$_3$, free base): 7.39–7.03 (m, 10H), 6.75–6.60 (m, 2H), 6.41 (d, J=2.2 Hz, 1H), 5.44 (br, 1H), 4.40 (d, J=12.5 Hz, 1H), 3.81–3.53 (m, 2H), 3.74 (s, 3H), 3.59 (s, 3H), 3.33–2.91 (m, 8H), 2.74–2.62 (m, 10H), 2.22 (br, 1H), 1.90–1.76 (m, 1H), 1.42–1.25 (m, 1H), 1.12 (t, J=7 Hz, 3H).

EXAMPLE 42

(3R*,4 S*,5S*,6S*)-N,N-(3-oxa-1,5-pentylene)-5-(2,5-dimethoxybenzylamino)-6-diphenylmethyl-1-azabicyclo[2.2.2]octane-3-carboxamide M.p.: 164°–165° C.

IR (KBr): 2935, 1645, 1498, 1450, 1432, 1268, 1232, 1112, 1048, 1023, 704 cm$^{-1}$.

$^1$H NMR (CDCl$_3$): 7.36–7.05 (m, 10H), 6.68 (dd, J=2.9, 8.8 Hz, 1H), 6.62 (d, J=8.8 Hz, 1H), 6.36 (d, J=2.9 Hz, 1H), 4.51 (d, J=12.1 Hz, 1H), 3.73 (s, 3H), 3.48 (s, 3H), 3.80–3.00 (m, 13H), 2.89 (dd, J=4.1, 7.7 Hz, 1H), 2.86–2.57 (m, 3H), 2.08 (br, 1H), 1.83–1.34 (m, 2H).

EXAMPLE 43

(2R*,4R*,5R*,6R*)-Methyl-6-diphenylmethyl-5-(2-methoxy-5-methylthiobenzylamino)-1-azabicyclo[2.2.2]octane-2-carboxylate dihydrochloride The title compound of Example 43 was treated in the same manner used for the preparation of compound 66 (Ex. 35).

M.p.: 132°–136° C.

IR (KBr): 3440, 1720, 1495 cm$^{-1}$.

$^1$H NMR (CDCl$_3$, free amine): 7.34–7.03 (m, 11H), 6.74 (d, J=2.6 Hz, 1H), 6.65 (d, J=8.4 Hz, 1H), 4.54 (d, J=11.7 Hz, 1H), 3.69–3.47 (s, 3H), 3.60 (s, 3H), 3.54 (s, 3H), 3.20 (d, J=13.2 Hz, 1H), 3.12–2.96 (m, 1H), 2.90 (dd, J=4.0, 8.1 Hz, 1H), 2.70–2.56 (m, 1H), 2.42 (s, 3H), 2.23–2.10 (m, 2H), 1.95–1.80 (m, 1H), 1.73–1.60 (m, 1H), 1.32–1.20 (m, 1H).

EXAMPLE 44

(2R*,4R*,5R*,6R*)-6-Diphenylmethyl-2-hydroxymethyl-5-(2-methoxy-5-methylthiobenzylamino)-1-azabicyclo[2.2.2]octane dihydrochloride The title compound of Example 44 was treated in the same manner used for the preparation of compound 67 (Ex. 36).

M.p.: 148°–452° C.

IR (KBr): 3420, 3200, 1495, 1250 cm$^{-1}$.

$^1$H NMR (CDCl$_3$, free amine): 7.40–6.96 (m, 11H), 6.76 (d, J=2.6 Hz, 1H), 6.65 (d, J=8.4 Hz, 1H), 4.61 (d, J=12.1 Hz, 1H), 3.63–3.37 (m, 4H), 3.51 (s, 3H), 3.23 (d, J=13.2 Hz, 1H), 3.04–2.90 (m, 3H), 2.60–2.47 (m, 1H), 2.41 (s, 3H), 2.10–1.75 (m, 3H), 2.72–2.58 (m, 1H), 1.12–0.98 (m, 2H).

EXAMPLE 45

(3R*,4S*,5S*,6S*)-N-Ethyl-5-(2,5-dimethoxybenzylamino)-6-diphenylmethyl-1-azabicyclo[2.2.2]octane-3-carboxamide The title compound of Example 45 was treated in the same manner used for the preparation of (3R*,4S*,5S*,6S*)-N-methoxy-N-methyl-5-(2,5-dimethoxybenzylamino)-6-diphenylmethyl-1-azabicyclo[2.2.2]octane-3-carboxamide (Ex. 41).

IR (KBr): 2490, 1645, 1498, 1463, 1451, 1228, 1047, 703 cm$^{-1}$.

$^1$H NMR (CDCl$_3$, free base): 7.39–7.06 (m, 10H), 6.80–6.65 (m, 2H), 6.38 (d, J=2 Hz, 1H), 5.39 (br, 1H), 4.48 (d, J=12 Hz, 1H), 3.74 (s, 3H), 3.55 (s, 3H), 3.64–2.50 (m, 11H), 2.22 (br, 1H), 1.86–1.44 (m, 2H).

EXAMPLE 46

(3R*,4S*,5S*,6S*)-N,N-(3-Thia-1,5-pentylene)-5-(2,5-dimethoxybenzylamino)-6-diphenylmethyl-1-azabicyclo[2.2.2]octane-3-carboxamide The title compound of Example 46 was treated in the same manner used for the preparation of compound 49 (Ex. 19).

M.p.: 185°–188° C.

IR (KBr): 2930, 1645, 1497, 1450, 1429, 1285, 1264, 1230, 1218, 1204, 1184, 1046, 1023, 802, 764, 703 cm$^{-1}$.

$^1$H NMR (CDCl$_3$): 7.36–7.04 (m, 10H), 6.70–6.59 (m, 2H), 6.36 (d, J=3 Hz, 1H), 4.52 (d, J=12 Hz, 1H), 4.18 (br, 2H), 3.72 (s, 3H), 3.48 (s, 3H), 3.87–3.43 (m, 4H), 3.35–2.47 (m, 11H), 2.11 (br, 1H), 1.84–1.54 (m, 2H).

EXAMPLE 47

(3R*,4S*,5S*,6S*)-N,N-(3-Thia-1,5-pentylene)-5-(2,5-dimethoxybenzylamino)-6-diphenylmethyl-1-azabicyclo[2.2.2]octane-3-carboxamide-S-oxide A mixture of (3R*,4S*,5S*,6S*)-N,N-(3-thia-1,5-pentylene)-5-(2,5-dimethoxybenzyl-amino)-6-diphenylmethyl-1-azabicyclo[2.2.2]octane-3-carboxamide (Ex. 46, 170 mg, 0.3 mmol), NaIO$_4$ (60 mg, 0.3 mmol), and H$_2$O (4 ml) was stirred at room temperature for 2 hours. The mixture was basified with NaHCO$_3$, extracted with CH$_2$Cl$_2$ (20 ml×2), dried and concentrated. The crude product was purified by a column chromatography (Silica gel 5 g, CH₂Cl₂:MeOH=10:1) and recrystallized from EtOH (10 ml) to give the title compound (70 mg, 40%).

M.p.: 235°–239° C.

IR (KBr): 3445, 2930, 1642, 1500, 1468, 1450, 1428, 1227, 1180, 1046, 1013, 748, 704 cm⁻¹.

¹H NMR (CDCl₃): 7.40–7.07 (m, 10H), 6.72–6.61 (m, 2H), 6.35 (d, J=3 Hz, 1H), 3.74 (s, 3H), 3.51 (s, 3H), 4.14–3.12 (m, 4H),3.00–2.54 (m, 11H), 2.11 (br, 1H), 1.85–1.55 (m, 2H).

EXAMPLE 48

(3R*,4S*,5S*,6S*)-N,N-(3-Thia-1,5-pentylene)-5-(2,5-dimethoxybenzylamino)-6-diphenylmethyl-1-azabicyclo[2.2.2]octane-3-carboxamide-S,S-dioxide A mixture of (3R*,4S*,5S*,6S*)-N,N-(3-thia-1,5-pentylene)-5-(2,5-dimethoxybenzylamino)-6-diphenylmethyl-1-azabicyclo[2.2.2]octane-3-carboxamide (Ex. 46, 200 mg, 0.35 mmol), potassium peroxymmonosulfate (620 mg, 1 mmol), MeOH (3 ml) and H₂O (3 ml) was stirred at room temperature for 5 hours. The mixture was basofied with NaHCO₃, extracted with CH₂Cl₂ (20 ml×3), dried and concentrated. The crude product was purified by a column chromatography (Silica gel 5 g, CH₂Cl₂:MeOH= 10:1) and recrystallized from EtOH (50 ml) to give the title compound (190 mg, 90%).

M.p.: 252°–254° C.

IR (KBr): 3435, 1648, 1500, 1317, 1283, 1229, 1192 cm⁻¹.

¹H NMR (CDCl₃): 7.40–7.07 (m, 10H), 6.73–6.61 (m, 2H), 6.32 (d, J=3 Hz, 1H), 4.52 (d, J=12 Hz, 1H), 4.48–4.30 (m, 2H), 3.74 (s, 3H), 3.48 (s, 3H), 3.90–2.55 (m, 15H), 2.02 (br, 1H), 1.83–1.46 (m, 2H).

EXAMPLE 49

(3R,4S,5S,6S)-5-(5-isopropyl-2-methoxybenzylamino)-6-diphenylmethyl-1-azabicyclo[2.2.2]octane-3-carboxamide dihydrochloride Optical resolution of (3R*,4R*)-N,N-Diethyl-5-oxo-1-azabicyclo[2.2.2]octane-3-carboxamide.

(3R*,4R*)-N,N-Diethyl-5-oxo-1-azabicyclo[2.2.2] octane-3-carboxamide (180 g, 0.804 mol) and (−)-dibenzoyl-L-tartaric acid (L-DBT) monohydrate (211 g, 0.561 mol) were added to ethanol (3.65 L), and the resultant mixture was heated at reflux until a clear solution was obtained. The solution was rapidly cooled down to c.a. 40° C. in a water-bath, and allowed to stand overnight to form crystals, which were collected by filtration. The obtained crystals (100.5 g, 21.5%) were found to be (+)-(3R,4R)-N,N-diethyl-5-oxo-1-azabicyclo[2.2.2]-octane-3-carboxamide L-DBT salt with 97% optical purity. An additional amount of (−)-L-DBT monohydrate (90.6 g, 0.241 mol) was added to the mother liquor, which was concentrated to c.a. 3.5 L by evaporation. The resulting mixture was heated at reflux to give a clear solution, which was allowed to stand at room temperature. After 2 days, formed crystals were collected by filtration. The crystals (117 g, 25%) were found to be (−)-(3S,4S)-N,N-diethyl-5-oxo-1-azabicyclo[2.2.2]-octane-3-carboxamide L-DBT salt with 92% optical purity. The same resolution process was repeated starting from 220 g of (3R*,4R*)-N,N-diethyl-5-oxo-1-azabicyclo[2.2.2]-octane-3-carboxamide. From this run, the L-DBT salt of the (+) enantiomer (180 g, 31%) with 95% optical purity and the L-DBT salt of the (−) enantiomer (91 g, 16%) with 97% optical purity were obtained. The L-DBT salt of the (−) enantiomer from the above two runs were combined, and suspended in 1.5 l of ethanol. The resulting suspension was heated at reflux for 3 hours, and allowed to stand overnight at room temperature. The obtained crystals were converted to the free amine by base treatment (aqueous bicarbonate) followed by extraction with methylene chloride to afford (−)-(3S,4S)-N,N-diethyl-5-oxo-1-azabicyclo[2.2.2]-octane-3-carboxamide (73 g, 18%) having greater than 99% optical purity. Similarly, 83 g of of the (+) enantiomer (21%) was obtained with greater than 99% optical purity. The above mentioned optical purities were determined using a chiral HPLC. The absolute configuration was determined by X-ray crystallography of the dibenzoyl-L-tartaric acid salt of the (−) enantiomer.

(3R,4R)-N,N-Diethyl-5-oxo-1-azabicyclo[2.2.2] octane-3-carboxamide (69) dibenzoyl-L-tartaric acid salt M.p.: 120°–135° C. (dec, no clear mp).

Analysis calc'd.: C, 60.27%; H, 6.48%; N, 4.39%. Found: C, 60.10%; H, 6.43%; N, 4.45%.

(+)-(3R,4R)-N,N-Diethyl-5-oxo-1-azabicyclo[2.2.2] octane-3-carboxamide (69)

M.p.: 108.6°–112.1° C. (ethyl acetate).

Analysis calc'd.: C, 64.26%; H, 8.99%; N, 12.49%; Found: C, 63.96%; H, 9.24%; N, 12.38%.

[α]_D=+59.0° (c=1.00, ethanol).

(3S,4S)-N,N-Diethyl-5-oxo-1-azabicyclo[2.2.2] octane-3-carboxamide (70) dibenzoyl-L-tartaric acid salt M.p.: 158.7°–159.3° C. (dec.).

Analysis calc'd.: C, 61.85%; H, 5.88%; N, 4.81%. Found: C, 61.64%; H, 5.91%; N, 4.81%.

(−)-(3S,4S)-N,N-Diethyl-5-oxo-1-azabicyclo[2.2.2] octane-3-carboxamide (70)

M.p.: 108.6°–111.5° C. (ethyl acetate).

Analysis calc'd.: C, 64.26%; H, 8.99%; N, 12.49%. Found C, 63.90%; H, 9.24%; N, 12.33%.

[α]_D^{25}=−58.8° (c=1.00, ethanol).

The title compound is an optical isomer of the title compound of Example 31 and was prepared from 70 in a manner similar to those described in Examples 5, 9, 19 and 20.

M.p.: 215°–219° C.

IR (KBr): 3320, 3200, 1685, 1505, cm⁻¹.

¹H NMR (270 MHz, CDCl₃, ppm): 7.35–7.00 (m, 11H), 6.67 (d, J=8.4 Hz, 1H), 6.57 (d, J=2.8 Hz, 1H), 5.57–5.36 (m, 2H), 4.48 (d, J=11.7 Hz, 1H), 3.70–3.62 (m, 2H), 3.55 (s, 3H), 3.26–2.90 (m, 5H), 2.80–2.26 (m, 2H), 2.51–2.40 (m, 2H), 1.92–1.80 (m, 1H), 1.70–1.66 (m, 1H), 1.21 (d, J=7.0 Hz, 3H), 1.18 (d, J=7.0 Hz, 3H).

[α]_D^{25}=+15.5° (c=1.00, DMSO)

EXAMPLE 50

(3R,4S,5S,6S,)-5-(5-isopropyl-2-methoxybenzylamino)-6-diphenylmethyl-1-azabicyclo[2.2.2]octane-3-carboxylic acid dihydrochloride The title compound is an optical isomer of the title compound of Example 32, and was prepared from the title compound of Example 49 in a manner similar to that described in Example 21.

M.p.: >230° C.

IR: (KBr): 3400, 3200, 1735, 1500 cm$^{-1}$.

$^1$H NMR (270 MHz, CDCl$_3$, ppm, free base): 7.40–6.98 (m, 11H), 6.63 (d, J=8.8 Hz, 1H), 6.57 (s, 1H), 4.45 (d, J=12.4 Hz, 1H), 3.50 (s, 3H), 3.97–3.80 (m, 1H), 3.64 (d, J=12.4 Hz, 1H), 3.50–3.00 (m, 6H), 2.90–2.50 (m, 4H), 1.97–1.82 (m, 1H), 1.70–1.52 (m, 1H), 1.19 (d, J=7.0 Hz, 3H), 1.17 (d, J=7.0 Hz, 3H).

$[\alpha]_D^{25}$=+9.90° (c=1.00, EtOH).

EXAMPLE 51

(3R,4S,5S,6S)-5-(2-Methoxy-5-methylthiobenzylamino)-6-diphenylmethyl-1-azabicyclo[2.2.2]octane-3-carboxamide dihydrochloride The title compound is an optical isomer of the title compound of Example 33, and was prepared from 70 in a manner similar to those described in Examples 9, 19 and 20.

M.p.: 218°–225° C.

IR (KBr): 3300, 3200, 1690, 1495 cm$^{-1}$.

$^1$H NMR (270 MHz, CDCl$_3$, ppm): 7.33–7.10 (11H, m), 6.72 (1H, d, J=2.6 Hz), 6.67 (d, J=8.4 Hz, 1H), 5.76 (s, 1H), 5.42 (br s, 1H), 4.46 (d, J=12.1 Hz, 1H), 3.85–3.74 (m, 1H), 3.61–3.56(m, 1H), 3.55(s, 1H), 3.28–2.98 (m, 5H), 2.80–2.43 (m, 3H), 2.42 (s, 3H), 1.92–1.65 (m, 2H).

$[\alpha]_D^{25}$=+20.8° (c=0.50, DMSO).

EXAMPLE 52

(3R,4S,5S,6S,)-5-(2-Methoxy-5-methylthiobenzylamino)-6-diphenylmethyl-1-azabicyclo[2.2.2]octane-3-carboxylic acid dihydrochloride The title compound is an optical isomer of the title compound of Example 30, and was prepared from the title compound of Example 51 in a manner similar to that described in Example 21.

M.p.: 212°–215° C.

IR: (KBr): 3400, 3200, 1720, 1495 cm$^{-1}$.

$^1$H NMR (270 MHz, CDCl$_3$, ppm, free base): 7.45–7.10 (m, 11H), 6.72 (s, 1H), 6.65 (d, J=8.8 Hz, 1H), 4.47 (d, J=11.0 Hz, 1H), 3.53 (s, 3H), 3.62–2.62 (m, 11H), 2.41 (s, 3H), 2.04–1.90 (m, 1H), 1.82–1.62 (m, 1H).

$[\alpha]_D^{25}$=+12.0° (c=1.00, DMSO).

EXAMPLE 53

(3R,4S,5S,6S)-5-(2,5-Dimethoxybenzylamino)-6-diphenylmethyl-1-azabicyclo[2.2.2]octane-3-carboxamide dihydrochloride The title compound is an optical isomer of the title compound of Example 20, and was prepared from 70 in a manner similar to those described in Example 5, 9, 19 and 20.

M.p.: 191°–196° C.

IR (KBr): 3300, 3200, 1685, 1505, cm$^{-1}$.

$^1$H NMR (270 MHz, CDCl$_3$, ppm): 7.33–7.08 (m, 10H), 6.71–6.62 (m, 2H), 6.35 (d, J=2.9 Hz, 1H), 5.44 (br s, 2H), 4.46 (d, J=12.1 Hz, 1H), 3.73 (s, 3H), 3.53 (s, 3H), 3.70–3.45 (m, 2H), 3.30–2.93 (m, 5H), 2.75–2.60 (m, 1H), 2.54–2.38 (m, 2H), 1.93–1.77 (m, 1H), 1.70–1.55 (m, 1H).

$[\alpha]_D^{25}$=+18.6° (c=0.50, DMSO).

EXAMPLE 54

(3R,4S,5S,6S,)-5-(2,5-Dimethoxybenzylamino)-6-diphenylmethyl-1-azabicyclo[2.2.2]octane-3-carboxylic acid dihydrochloride The title compound is an optical isomer of the title compound of Example 21, and was prepared from the title compound of Example 53 in a manner similar to that described in Example 21.

M.p.: 238°–245° C.

IR: (KBr): 3500, 1720, 1505, 1440 cm$^{-1}$.

$^1$H NMR (270 MHz, CDCl$_3$, ppm, free base): 7.32–7.02 (m, 10H), 6.71–6.56 (m, 2H), 6.41 (br s, 1H), 4.38 (d, J=11.0 Hz, 1H), 3.68 (s, 3H), 3.90–3.45 (m, 2H), 3.44 (s, 3H), 3.25–2.95 (m, 4H), 2.74–2.20 (m, 5H), 1.90–1.55 (m, 2H).

$[\alpha]_D^{25}$=+12.7° (c=1.00, DMSO).

EXAMPLE 55

(3S,4R,5R,6R)-5-Isopropyl-2-methoxybenzylamino)-6-diphenylmethyl-1-azabicyclo[2.2.2]octane-3-carboxamide dihydrochloride The title compound is an optical isomer of the title compound of Example 31 and was prepared from 69 in a manner similar to those described in Examples 5, 9, 19 and 20.

M.p.: 246°–249° C.

Analysis calc'd.: C, 63.35%; H, 7.48%; N, 6.93%, (2H$_2$O). Found: C, 63.16%; H, 7.54%, N, 6.93%.

$[\alpha]_D^{25}$=−15.0° (c=1.00, DMSO).

EXAMPLE 56

(3S,4R,5R,6R,)-5-(5-Isopropyl-2-methoxybenzylamino)-6-diphenylmethyl-1-azabicyclo[2.2.2]octane-3-carboxylic acid dihydrochloride The title compound is an optical isomer of the title compound of Example 32, and was prepared from the title compound of Example 55 in a manner similar to that described in Example 21.

M.p.: 210°–213° C.

Analysis calc'd.: C, 64.21%; H: 7.24%; N, 4.68% (1.5H$_2$O). Found: C, 64.32%; H, 7.33%; N, 4.89%

$[\alpha]_D^{25}$=−9.80° (c=1.00, EtOH).

EXAMPLE 57

(2R*,4R*,5R*,6R*)-6-Diphenylmethyl-5-(5-isopropyl-2-methoxybenzylamino)-1-azabicyclo[2.2.2]octane-2-carboxylic acid dihydrochloride The title compound was prepared in a manner similar to those described in Examples 15 and 21.

M.p.: 138°–141° C.

IR (KBr): 3420, 2970, 1740, 1510 cm$^{-1}$.

$^1$H NMR (270 MHZ, CDCl$_3$, ppm, free base): 7.41–7.14 (m, 10H), 7.08 (dd, J=2.6, 8.4 Hz, 1H), 6.66 (d, J=8.4 Hz, 1H), 6.60 (d, J=2.6 Hz, 1H), 4.68 (d, J=12.1 Hz, 1H), 4.32 (dd, J=8.8 and 12.1 Hz, 1H), 3.90–3.78 (m, 1H), 3.50 (s, 3H), 3.42–3.33 (m, 2H), 3.30–3.22 (m, 2H), 2.90–2.72 (m, 1H), 2.65–2.55 (m, 1H), 2.46–2.35 (m, 1H), 2.23–2.14 (m, 1H), 2.09–1.92 (m, 1H), 1.73–1.56 (m, 1H), 1.21 (d, J=7.0 Hz, 3H), 1.20 (d, J=7.0 Hz, 3H), 1.20 (d, J=7.0 Hz, 3H).

We claim:

1. A compound having the formula

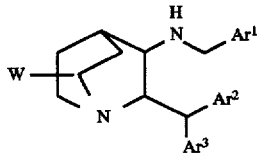

(I)

wherein W is Y or $X(CH_2)_n$;

Y is optionally substituted $(C_1-C_6)$alkyl, optionally substituted $(C_2-C_6)$alkenyl or optionally substituted $(C_3-C_8)$cycloalkyl;

X is optionally substituted $(C_1-C_6)$alkoxy, hydroxy, $CO_2R^1$, $CHR^1OR^2$, $CHR^1NR^2R^3$, $COR^1$, or optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and n is an integer from zero to six;

$Ar^1$, $Ar^2$ and $Ar^3$ are each, independently, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl;

and $R^1$, $R^2$ and $R^3$ are independently selected from hydrogen, optionally substituted $(C_1-C_6)$alkyl, optionally substituted $(C_1-C_6)$alkoxy, optionally substituted $(C_3-C_8)$cycloalkyl, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and optionally substituted $(C_1-C_5)$heterocyclic groups, wherein said heterocyclic groups are selected from pyrrolidino and piperidino;

and wherein the substituents on the foregoing substituted alkyl, alkenyl, cycloalkyl and alkoxy groups are independently selected from halo, nitro, amino, $(C_1-C_4)$alkyl, $(C_1-C_4)$alkoxy, trifluoromethyl and trifluoromethoxy;

and wherein the substituents on the foregoing substituted $(C_1-C_5)$ heterocyclic groups are attached to a sulfur or nitrogen atom on the ring and are independently selected from oxygen, di-oxygen and $(C_1-C_4)$alkyl when attached to a ring sulfur atom, and are independently selected from oxygen and $(C_1-C_4)$alkyl when attached to a ring nitrogen atom;

and wherein the substituents on said substituted $Ar^1$ groups are independently selected from $(C_1-C_6)$alkyl optionally substituted with from one to three halo groups, $(C_1-C_6)$alkoxy optionally substituted with from one to three halo groups, $(C_1-C_6)$alkylsulfinyl, $(C_2-C_6)$ alkenyl, $(C_1-C_6)$alkylthio, $(C_1-C_6)$ alkylsulfonyl, $(C_1-C_6)$alkylsulfonylamino, and di-$(C_1-C_6)$alkylamino wherein one or both of the alkyl groups may be optionally substituted with a $(C_1-C_6)$ alkylsulfonyl, or $(C_1-C_6)$alkylsulfinyl group;

and wherein the substituents on said substituted $Ar^2$ and $Ar^3$ groups are independently selected from $(C_1-C_4)$ alkyl, $(C_1-C_4)$alkoxy, $(C_1-C_4)$alkylthio, $(C_1-C_4)$ alkylsulfinyl, di-$(C_1-C_4)$alkylamino, trifluoromethyl and trifluoromethoxy;

with the proviso that: (a) Y can not be (i) unsubstituted straight or branched $(C_1-C_6)$alkyl, (ii) unsubstituted straight or branched $(C_2-C_6)$alkenyl, (iii) straight or branched $(C_1-C_6)$alkyl substituted with $(C_1-C_4)$alkyl, or (iv) straight or branched $(C_2-C_6)$alkenyl substituted with $(C_1-C_4)$alkyl;

or a pharmaceutically acceptable salt of such compound.

2. A compound according to claim 1 wherein W is $X(CH_2)_n$.

3. A compound according to claim 1 wherein W is Y.

4. A compound according to claim 2 wherein $Ar^1$ is substituted aryl.

5. A compound according to claim 4 wherein $Ar^1$ is mono-, di- or tri-substituted phenyl.

6. A compound according to claim 5 wherein $Ar^1$ is phenyl disubstituted at the 2- and 5-positions.

7. A compound according to claim 5 wherein $Ar^1$ is paramethoxyphenyl and each of $Ar^2$ and $Ar^3$ is phenyl.

8. A compound according to claim 7 wherein X is phenyl.

9. A compound according to claim 7 wherein X is dialkylaminomethyl.

10. A compound according to claim 7 wherein X is carboxylic acid.

11. A compound according to claim 7 wherein X is alkoxycarbonyl.

12. A compound according to clam 7 wherein X is hydroxymethyl.

13. A compound according to claim 1, wherein said compound is selected from the group consisting of:

(3R,4S,5S,6S)-N,N-diethyl-5-(5-isopropyl-2-methoxybenzylamino)-6-diphenylmethyl-1-azabicyclo [2.2.2]octane-3-carboxamide;

(3R,4S,5S,6S)-N,N-diethyl-5-(2,5-dimethoxybenzyl-amino)-6-diphenylmethyl-1-azabicyclo[2.2.2]octane-3-carboxamide;

(3R,4S,5S,6S)-5-(5-isopropyl-2-methoxybenzylamino)-6-diphenylmethyl-1-azabicyclo[2.2.2]octane-3-carboxylic acid;

(3R,4S,5S,6S)-5-(2-methoxy-5-methylthiobenzylamino)-6-diphenylmethyl-1-azabicyclo[2.2.2]octane-3-carboxylic acid;

(3R,4S,5S,6S)-5-(2,5-dimethoxybenzylamino)-6-diphenylmethyl-1-azabicyclo[2.2.2]octane-3-carboxylic acid;

(3R,4S,5S,6S)-5-(2-methoxy-5-methylbenzylamino)-6-diphenylmethyl-1-azabicyclo[2.2.2]octane-3-carboxylic acid;

(3R,4S,5S,6S)-5-(5-ethyl-2-methoxybenzylamino)-6-diphenylmethyl-1-azabicyclo[2.2.2]octane-3-carboxylic acid;

(3R,4S,5S,6S)-5-(2-methoxyl-5-n-propylbenzylamino)-6-diphenylmethyl-1-azabicyclo[2.2.2]octane-3-carboxylic acid;

(3R,4S,5S,6S)-5-(5-sec-butyl-2-methoxybenzylamino)-6-diphenylmethyl-1-azabicyclo [2.2.2]octane-3-carboxylic acid;

(3R,4S,5S,6S)-5-(5-N-methyl-methanesulfonylamino-2-methoxybenzylamino)-6-diphenylmethyl-1-azabicyclo [2.2.2]octane-3-carboxylic acid;

(3R,4S,5S,6S)-5-(2-methoxy-5-methylsulfinylbenzylamino)-6-diphenylmethyl-1-azabicyclo[2.2.2]octane-3-carboxylic acid;

(3R,4S,5S,6S)-5-(2-methoxy-5-trifluoromethoxybenzylamino)-6-diphenylmethyl-1-azabicyclo[2.2.2]octane-3-carboxylic acid;

(3R,4S,5S,6S)-5-(2-methoxy-5-methylsulfonylbenzylamino)-6-diphenylmethyl-1-azabicyclo[2.2.2]octane-3-carboxylic acid;

(3R,4S,5S,6S)-5-(5-dimethylamino-2-methoxybenzylamino)-6-diphenylmethyl-1-azabicyclo[2.2.2]octane-3-carboxylic acid;

(2S,4S,5S,6S)-5-(5-isopropyl-2-methoxybenzylamino)-6-diphenylmethyl-1-azabicyclo[2.2.2]octane-2-carboxylic acid;

(2S,4S,5S,6S)-5-(2-methoxy-5-methylthiobenzylamino)-6-diphenylmethyl-1-azabicyclo[2.2.2]octane-2-carboxylic acid;

(2S,4S,5S,6S)-5-(2,5-dimethoxybenzylamino)-6-diphenylmethyl-1-azabicyclo[2.2.2]octane-2-carboxylic acid;

(2S,4S,5S,6S)-5-(2-methoxy-5-methylbenzylamino)-6-diphenylmethyl-1-azabicyclo[2.2.2]octane-2-carboxylic acid;

(2S,4S,5S,6S)-5-(5-ethyl-2-methoxybenzylamino)-6-diphenylmethyl-1-azabicyclo[2.2.2]octane-2-carboxylic acid;

(2S,4S,5S,6S)-5-(2-methoxyl-5-n-propylbenzylamino)-6-diphenylmethyl-1-azabicyclo[2.2.2]octane-2-carboxylic acid;

(2S,4S,5S,6S)-5-(5-sec-butyl-2-methoxybenzylamino)-6-diphenylmethyl-1-azabicyclo[2.2.2]octane-2-carboxylic acid;

(2S,4S,5S,6S)-5-(5-N-methyl-methanesulfonylamino-2-methoxybenzylamino)-6-diphenylmethyl-azabicyclo[2.2.2]octane-2-carboxylic acid;

(2S,4S,5S,6S)-5-(2-methoxy-5-methylsulfinylbenzylamino)-6-diphenylmethyl-1-azabicyclo [2.2.2]octane-2-carboxylic acid;

(2S,4S,5S,6S)-5-(2-methoxy-5-trifluoromethoxybenzylamino)-6-diphenylmethyl-1-azabicyclo[2.2.2]octane-2-carboxylic acid;

(2S,4S,5S,6S)-5-(2-methoxy-5-methylsulfonylbenzylamino)-6-diphenylmethyl-1-azabicyclo[2.2.2]octane-2-carboxylic acid; and (2S,4S,5S,6S)-5-(5-dimethylamino-2-methoxybenzylamino)-6-diphenylmethyl-1-azabicyclo[2.2.2]octane-2-carboxylic acid.

14. A compound according to claim 2, having the formula

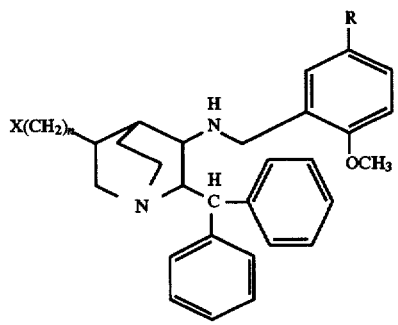

wherein R is halo, ($C_1$–$C_6$)alkyl optionally substituted with from one to three halo groups, ($C_1$–$C_6$)alkoxy optionally substituted with from one to three halo groups, ($C_2$–$C_6$) alkenyl, ($C_1$–$C_6$)alkylthio, ($C_1$–$C_6$)alkylsulfinyl, ($C_1$–$C_6$) alkylsulfonyl; n is an integer from zero to six; and X is optionally substituted ($C_1$–$C_6$)alkoxy, $CO_2R^1$, $CHR^1OR^2$, $CHR^1NR^2R^3$, $COR^1$, or optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; $R^1$, $R^2$ and $R^3$ are each independently selected from hydrogen, optionally substituted ($C_1$–$C_5$)alkyl, optionally substituted ($C_1$–$C_6$)alkoxy, optionally substituted ($C_3$–$C_8$)cycloalkyl, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and optionally substituted ($C_1$–$C_5$) heterocyclic groups, wherein said heterocyclic groups are selected from pyrrolidino and piperidino.

15. A compound according to claim 2, having the formula

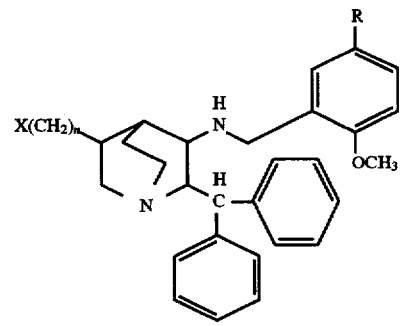

wherein R is hydrogen, chloro, methyl, ethyl, n-propyl, i-propyl, sec-butyl, t-butyl, methoxy, methylthio, N-methyl-N-methylsulfonylamino, methylsulfinyl, methylsulfonyl, trifluoromethoxy, dimethylamino; n is an integer from zero to two; and X is phenyl, diethylaminomethyl, hydroxymethyl, carboxyl, methoxycarbonyl, or —$COR^4$ wherein $R^4$ is selected from groups having the formulae

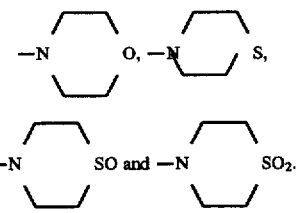

16. A compound according to claim 15, wherein the absolute configuration is (3R,4S,5S,6S), n is zero; and X is a carboxyl group.

17. A compound according to claim 15, wherein the absolute configuration is (3R,4S,5S,6S); n is 1; and X is a hydroxy group.

18. A compound of the formula

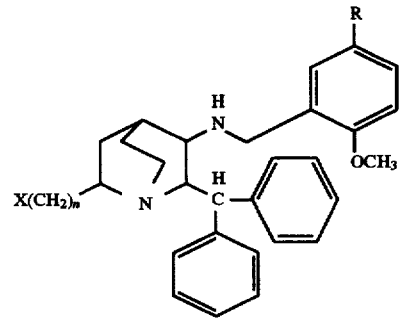

wherein R is halo, ($C_1$–$C_6$)alkyl optionally substituted with from one to three halo groups, ($C_1$–$C_6$)alkoxy optionally substituted with from one to three halo groups, ($C_2$–$C_6$) alkenyl, ($C_1$–$C_6$)alkylthio, ($C_1$–$C_6$)alkylsulfinyl, ($C_1$–$C_6$) alkylsulfonyl; n is an integer from zero to six; and X is optionally substituted ($C_1$–$C_6$)alkoxy, $CO_2R^1$, $CHR^1OR^2$, $CHR^1NR^2R^3$, $COR^1$, or optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; $R^1$, $R^2$ and $R^3$ are each independently selected from hydrogen, optionally substituted ($C_1$–$C_6$)alkyl, optionally substituted ($C_1$–$C_5$)alkoxy, optionally substituted ($C_3$–$C_8$)cycloalkyl, optionally substituted aryl, wherein said aryl is selected from phenyl, naphthyl, pyridyl, quinolyl, thienyl, furyl, phenoxyphenyl, oxazolyl, tetrazolyl, thiazolyl, imidazolyl and pyrazolyl; and optionally substituted ($C_1$–$C_5$) heterocyclic groups, wherein said heterocyclic groups are selected from pyrrolidino, piperidino, morpholino, piperazinyl and thiamorpholino.

19. A compound according to claim 18, wherein R is hydrogen, chloro, methyl, ethyl, n-propyl, i-propyl, sec-butyl, t-butyl, methoxy, methylthio, N-methyl-N-methylsulfonylamino, methylsulfinyl, methylsulfonyl, trifluoromethoxy, dimethylamino; n is an integer from zero to two; and X is phenyl, diethylaminomethyl, hydroxymethyl, carboxyl, methoxycarbonyl, or —$COR^4$ wherein $R^4$ is selected from groups having the formulae

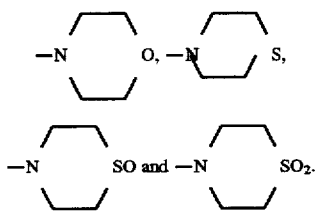

20. A compound according to claim 19, wherein the absolute configuration is (2S,4S,5S,6S), n is zero and X is a carboxyl group.

21. A compound according to claim 16, wherein R is an isopropyl group.

22. A compound according to claim 16, wherein R is a methoxy group.

23. A compound according to claim 16, wherein R is a methylthio group.

24. A compound according to claim 15, wherein the absolute configuration is (3S,4S,5S,6S); n is zero; and R is isopropyl group.

25. A compound according to claim 3 wherein $Ar^2$ and $Ar^3$ are phenyl groups.

26. A compound of the following chemical formula

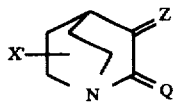

wherein X' is phenethyl or —$COR^4$; $R^4$ is hydroxy, —N-morpholine, —N-4-thiamorpholine or —$NR^5R^6$ and is substituted at 4-, 5- or 6-position on quinuclidine ring; $R^5$ and $R^6$ are each, independently, hydrogen, alkyl having from one to four carbon atoms or alkoxy having from one to four carbon atoms; Z is oxygen or ethylenedioxy; Q is benzylidene or benzhydryl.

27. A compound according to claim 26, selected from the group consisting of:

4-Allyl-2-benzylidene-1-azabicyclo[2.2.2]-octane-3-one;
4-Allyl-2-diphenylmethyl-1-azabicyclo[2.2.2]-octane-3-one;
4-Allyl-2-diphenylmethyl-1-azabicyclo[2.2.2]-octane-3-amine; and
4-Allyl-2-diphenylmethyl-1-azabicyclo[2.2.2]-octane-3-aminoaldehyde.

28. A pharmaceutical composition for treating or preventing a condition selected from the group consisting of inflammatory diseases, anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising an amount of a compound according to claim 1 effective in preventing or treating such condition and a pharmaceutically acceptable carrier.

29. A method of treating or preventing a condition selected from the group consisting of inflammatory diseases anxiety, colitis, depression or dysthymic disorders, psychosis, pain, allergies, chronic obstructive airways disease, hypersensitivity disorders, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment or prevention an amount of a compound according to claim 1 effective in preventing or treating such condition.

30. A pharmaceutical composition for antagonizing the effects of substance P in a mammal, comprising a substance P antagonizing effective amount of a compound according to claim 1 and a pharmaceutically acceptable carrier.

31. A method of antagonizing the effects of substance P in a mammal, comprising administering to said mammal a substance P antagonizing effective amount of a compound according to claim 1.

32. A pharmaceutical composition for treating or preventing a condition in a mammal, the treatment or prevention of which is effected or facilitated by a decrease in substance P mediated neurotransmission, comprising an amount of a compound according to claim 1 effective in antagonizing the effect of substance P at its receptor site and a pharmaceutically acceptable carrier.

33. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

34. A pharmaceutical composition for treating or preventing a condition in a mammal, the treatment or prevention of which is effected or facilitated by a decrease in substance P mediated neurotransmission, comprising an amount of a compound according to claim 1, or a pharmaceutically acceptable salt thereof, effective in treating or preventing such condition and a pharmaceutically acceptable carrier.

35. A method of treating or preventing a condition in mammal, the treatment or prevention of which is effected or facilitated by a decrease in substance P mediated neurotransmission, comprising administering to a mammal in need of such treatment or prevention an amount of a compound according to claim 1 effective in treating or preventing such condition.

* * * * *